United States Patent
Suzuki et al.

(10) Patent No.: US 10,081,598 B2
(45) Date of Patent: Sep. 25, 2018

(54) CATIONIC LIPID

(71) Applicants: Eisai R&D Management Co., Ltd., Tokyo (JP); Sogo Pharmaceutical Co., Ltd., Tokyo (JP)

(72) Inventors: Yuta Suzuki, Tsukuba (JP); Kenji Hyodo, Tsukuba (JP); Yohei Tanaka, Nakama (JP)

(73) Assignees: Eisai R&D Management Co., Ltd., Tokyo (JP); Sogo Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 15/533,576

(22) PCT Filed: Dec. 24, 2015

(86) PCT No.: PCT/JP2015/085969
§ 371 (c)(1),
(2) Date: Jun. 6, 2017

(87) PCT Pub. No.: WO2016/104580
PCT Pub. Date: Jun. 30, 2016

(65) Prior Publication Data
US 2017/0334852 A1    Nov. 23, 2017

(30) Foreign Application Priority Data

Dec. 26, 2014    (JP) .................................. 2014-266548

(51) Int. Cl.
| | | |
|---|---|---|
| *A61K 31/713* | (2006.01) |
| *C07D 211/62* | (2006.01) |
| *C12N 15/113* | (2010.01) |
| *C07C 229/06* | (2006.01) |
| *A61K 47/10* | (2017.01) |
| *A61K 47/22* | (2006.01) |
| *A61K 47/28* | (2006.01) |
| *C07C 229/12* | (2006.01) |
| *C12N 15/09* | (2006.01) |

(52) U.S. Cl.
CPC .......... *C07D 211/62* (2013.01); *A61K 31/713* (2013.01); *A61K 47/10* (2013.01); *A61K 47/22* (2013.01); *A61K 47/28* (2013.01); *C07C 229/06* (2013.01); *C07C 229/12* (2013.01); *C12N 15/1137* (2013.01); *C12N 15/09* (2013.01); *C12N 15/113* (2013.01); *C12N 2310/14* (2013.01)

(58) Field of Classification Search
CPC ...... A61K 31/713; A61K 47/22; C12N 15/09; C12N 15/113; C12N 2310/14; C07D 211/62
USPC ....... 435/6.1, 91.1, 91.31, 455, 458; 514/44; 536/23.1, 24.5
See application file for complete search history.

(56) References Cited

U.S. PATENT DOCUMENTS

| | | |
|---|---|---|
| 2012/0027803 A1 | 2/2012 | Manoharan et al. |
| 2016/0326116 A1 | 11/2016 | Suzuki et al. |

FOREIGN PATENT DOCUMENTS

| | | |
|---|---|---|
| JP | A-2012-530059 | 11/2012 |
| JP | A-2013-533224 | 8/2013 |
| WO | WO 2010/144740 | 12/2010 |
| WO | WO 2011/153493 | 12/2011 |
| WO | WO 2013/086354 | 6/2013 |
| WO | WO 2013/158579 | 10/2013 |
| WO | WO 2014/089239 | 6/2014 |
| WO | WO 2015/105131 | 7/2015 |

OTHER PUBLICATIONS

Extended European Search Report dated May 4, 2018 to the counterpart European application No. 15873148.9.
Suzuki et al., "Biodegradable lipid nanoparticles induce a prolonged RNA interference-mediated protein knockdown and show rapid hepatic clearance in mice and nonhuman primates", International Journal of Pharmaceutics, vol. 519, No. 1-2, Jan. 9, 2017, pp. 34-43.
International Search Report and Written Opinion in International Application No. PCT/JP2015/085969, dated Mar. 15, 2016, 13 pages (English Translation).

Primary Examiner — Jane J Zara
(74) Attorney, Agent, or Firm — Fish & Richardson P.C.

(57) ABSTRACT

The present invention provides a cationic lipid which can be utilized for nucleic acid delivery into the cytoplasm. The cationic lipid of the present invention is, for example, a compound represented by the following Formula (1) or a pharmaceutically acceptable salt thereof.

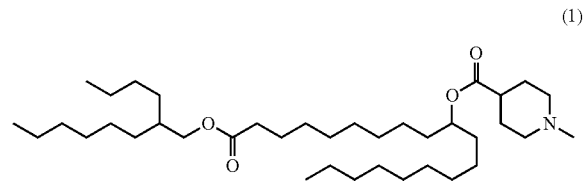

(1)

8 Claims, 2 Drawing Sheets
Specification includes a Sequence Listing.

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: siRNA sense sequence
<220> FEATURE:
<221> NAME/KEY: misc_feature
<222> LOCATION: (1)..(3)
<223> OTHER INFORMATION: RNA
<220> FEATURE:
<221> NAME/KEY: misc_feature
<222> LOCATION: (4)..(5)
<223> OTHER INFORMATION: fluoro RNA
<220> FEATURE:
<221> NAME/KEY: misc_feature
<222> LOCATION: (5)..(6)
<223> OTHER INFORMATION: RNA
<220> FEATURE:
<221> NAME/KEY: misc_feature
<222> LOCATION: (7)..(10)
<223> OTHER INFORMATION: fluoro RNA
<220> FEATURE:
<221> NAME/KEY: misc_feature
<222> LOCATION: (11)..(13)
<223> OTHER INFORMATION: RNA
<220> FEATURE:
<221> NAME/KEY: misc_feature
<222> LOCATION: (14)..(17)
<223> OTHER INFORMATION: fluoro RNA
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (19)..(19)
<223> OTHER INFORMATION: fluoro RNA
<220> FEATURE:
<221> NAME/KEY: misc_feature
<222> LOCATION: (20)..(21)
<223> OTHER INFORMATION: DNA
<220> FEATURE:
<221> NAME/KEY: misc_feature
<222> LOCATION: (20)..(21)
```

<223> OTHER INFORMATION: phosphorothioate linkage

<400> SEQUENCE: 1
ggaucaucuc aagucuuact t    21

<210> SEQ ID NO 2
<211> LENGTH: 21
<212> TYPE: DNA
<213> ORGANISM: Artificial Sequence
<220> FEATURE:
<223> OTHER INFORMATION: siRNA anti-sense sequence
<220> FEATURE:
<221> NAME/KEY: misc_feature
<222> LOCATION: (1)..(1)
<223> OTHER INFORMATION: RNA
<220> FEATURE:
<221> NAME/KEY: misc_feature
<222> LOCATION: (2)..(2)
<223> OTHER INFORMATION: fluoro RNA
<220> FEATURE:
<221> NAME/KEY: misc_feature
<222> LOCATION: (3)..(6)
<223> OTHER INFORMATION: RNA
<220> FEATURE:
<221> NAME/KEY: misc_feature
<222> LOCATION: (7)..(9)
<223> OTHER INFORMATION: fluoro RNA
<220> FEATURE:
<221> NAME/KEY: misc_feature
<222> LOCATION: (10)..(13)
<223> OTHER INFORMATION: RNA
<220> FEATURE:
<221> NAME/KEY: misc_feature
<222> LOCATION: (14)..(14)
<223> OTHER INFORMATION: fluoro RNA
<220> FEATURE:
<221> NAME/KEY: misc_feature
<222> LOCATION: (15)..(16)
<223> OTHER INFORMATION: RNA
<220> FEATURE:
<221> NAME/KEY: misc_feature
<222> LOCATION: (17)..(19)
<223> OTHER INFORMATION: fluoro RNA
<220> FEATURE:
<221> NAME/KEY: misc_feature
<222> LOCATION: (20)..(21)
<223> OTHER INFORMATION: DNA
<220> FEATURE:
<221> NAME/KEY: misc_feature
<222> LOCATION: (20)..(21)
<223> OTHER INFORMATION: phosphorothioate linkage

<400> SEQUENCE: 2
guaagacuug agaugaucct t    21

<210> SEQ ID NO 3
<211> LENGTH: 21
<212> TYPE: RNA
<213> ORGANISM: Artificial Sequence
<220> FEATURE:
<223> OTHER INFORMATION: siRNA sense sequence
<220> FEATURE:
<221> NAME/KEY: misc_feature
<222> LOCATION: (4)..(4)
<223> OTHER INFORMATION: 2'-Ome RNA
<220> FEATURE:
<221> NAME/KEY: misc_feature
<222> LOCATION: (10)..(10)
<223> OTHER INFORMATION: 2'-Ome RNA
<220> FEATURE:
<221> NAME/KEY: misc_feature
<222> LOCATION: (14)..(14)
<223> OTHER INFORMATION: 2'-Ome RNA
<220> FEATURE:
<221> NAME/KEY: misc_feature

```
<222> LOCATION: (18)..(18)
<223> OTHER INFORMATION: 2'-Ome RNA

<400> SEQUENCE: 3
agaucacccu ccuuaaauau u                                      21

<210> SEQ ID NO 4
<211> LENGTH: 21
<212> TYPE: RNA
<213> ORGANISM: Artificial Sequence
<220> FEATURE:
<223> OTHER INFORMATION: siRNA anti-sense sequence
<220> FEATURE:
<221> NAME/KEY: misc_feature
<222> LOCATION: (8)..(8)
<223> OTHER INFORMATION: 2'-Ome RNA
<220> FEATURE:
<221> NAME/KEY: misc_feature
<222> LOCATION: (17)..(17)
<223> OTHER INFORMATION: 2'-Ome RNA

<400> SEQUENCE: 4
uauuuaagga gggugaucuu u                                      21
```

CATIONIC LIPID

TECHNICAL FIELD

The present invention relates to a novel cationic lipid. Priority is claimed on Japanese Patent Application No. 2014-266548, filed on Dec. 26, 2014, the content of which is incorporated herein by reference.

BACKGROUND OF THE INVENTION

A nucleic acid such as small interfering RNA (siRNA), micro RNA (miRNA), a short hairpin RNA or small hairpin RNA (shRNA) expression vector, or antisense oligonucleotide is a nucleic acid that induces sequence-specific gene expression inhibition in vivo and is known as nucleic acid medicine.

In the field of nucleic acid medicine, particularly, siRNA has been attracting attention. siRNA is double-stranded RNA formed of 19 to 23 base pairs and induces sequence-specific gene expression inhibition referred to as RNA interference (RNAi).

Although siRNA is chemically stable, siRNA has problems as therapeutic applications since siRNA is easily decomposed by ribonuclease (RNase) in blood plasma and siRNA is unlikely to penetrate a cell membrane by itself (for example, see PTL 1).

For the above-described problems, it is known that by encapsulating siRNA in a fine particle containing a cationic lipid, the encapsulated siRNA is protected from decomposition in blood plasma and can penetrate a lipophilic cell membrane (for example, see PTL 1).

Further, PTLs 2 to 4 describe a cationic lipid that is used to deliver nucleic acid medicine such as siRNA and has improved biodegradability.

Further, fine particles containing a cationic lipid have a stability problem in that they are prone to aggregation during a storage period, and a method of suppressing aggregation by allowing a polyethylene glycol-modified lipid (PEG lipid) to be contained in the fine particles is known to solve this problem. Further, a method of suppressing aggregation and improving efficiency of nucleic acid delivery by using PEG-DPG; which is a specific PEG lipid, as a constituent component of fine particles or by using a formulation formed of PEG-DPG with the fine particles and a deionized solvent is described in PTL 5.

CITATION LIST

Patent Literature

[PTL 1] Published Japanese Translation No. 2012-530059 of the PCT International Publication
[PTL 2] Pamphlet of PCT International Publication No. WO2011/153493
[PTL 3] Pamphlet of PCT International Publication No. WO2013/086354
[PTL 4] Pamphlet of PCT International Publication No. WO2013/158579
[PTL 5] Pamphlet of PCT International Publication No. WO2014/089239

SUMMARY OF THE INVENTION

Technical Problem

However, despite the recent developments, a cationic lipid which can be utilized for nucleic acid delivery into the cytoplasm is still required.

Solution to Problem

The present invention relates to the following [1] to [8].

[1] A compound selected from the group consisting of compounds represented by the following Formulae (1) to (11) or a pharmaceutically acceptable salt thereof.

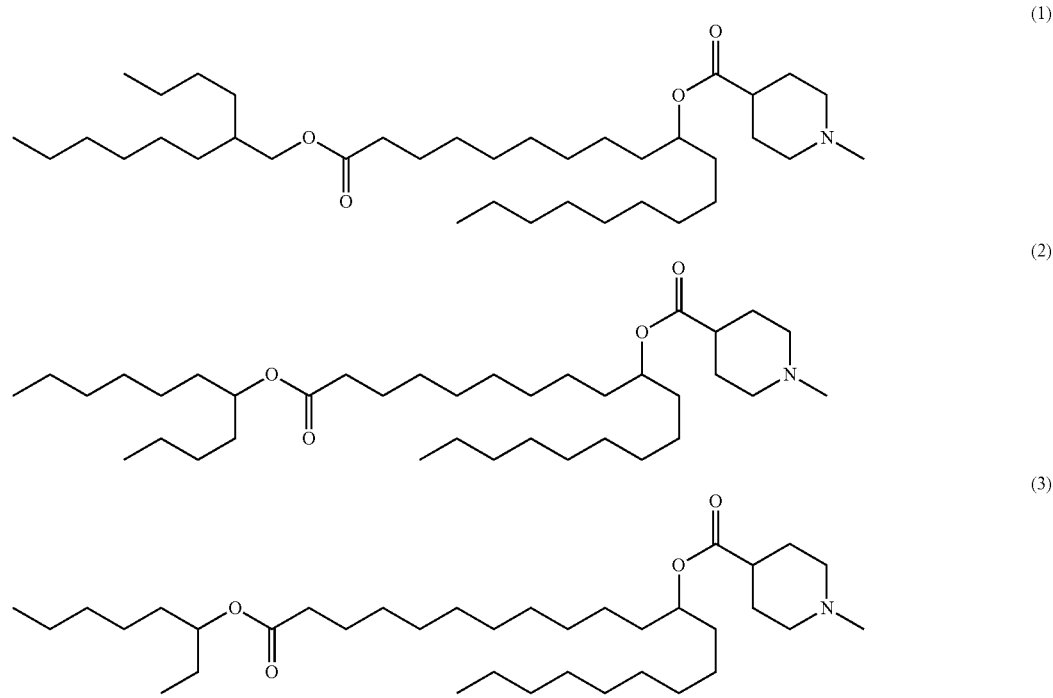

(4)
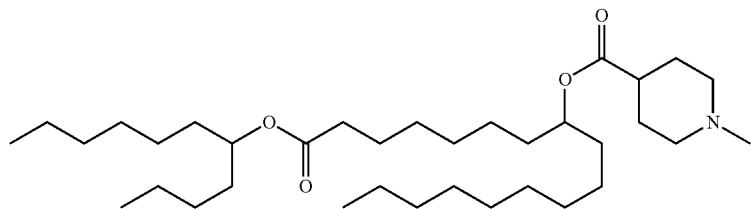
(5)
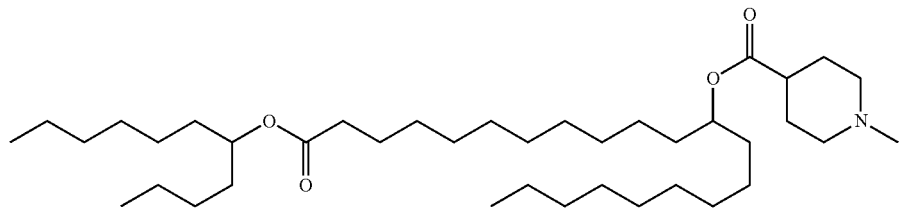
(6)
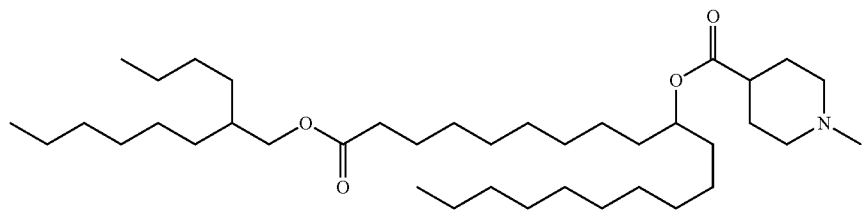
(7)
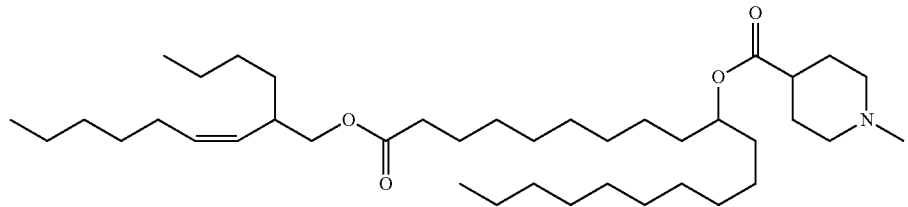
(8)
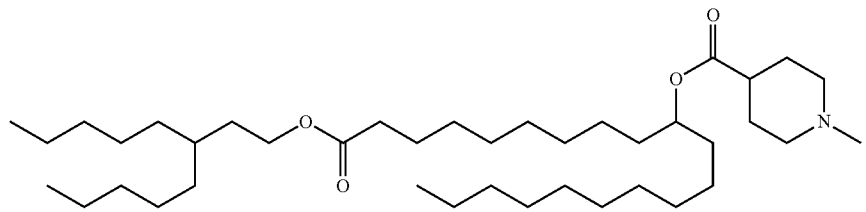
(9)
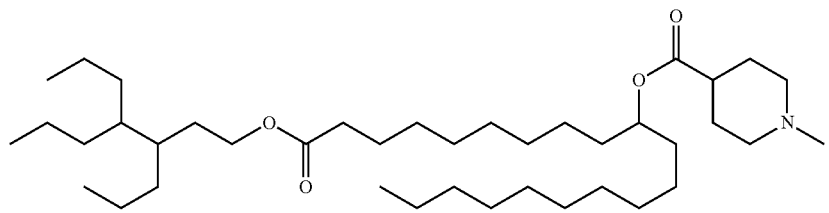
(10)
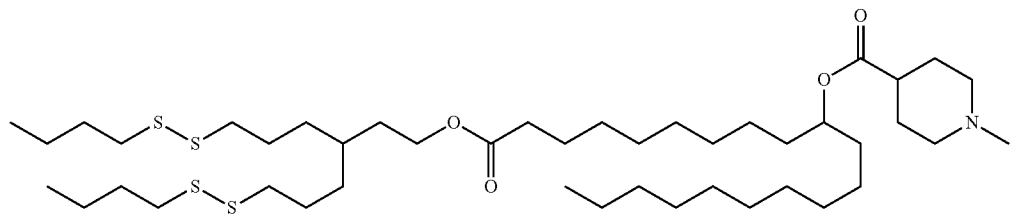

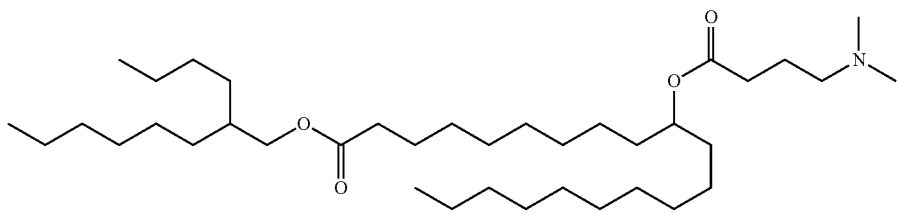
(11)
[2] The compound according to [1] selected from the group consisting of compounds represented by the following Formulae (1) and (6) to (9) or a pharmaceutically acceptable salt thereof.
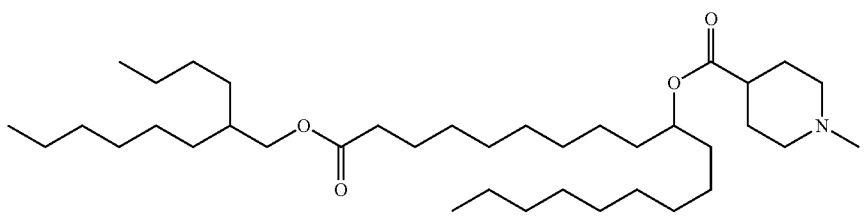
(1)
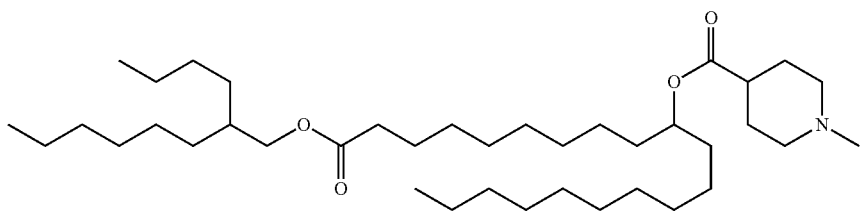
(6)
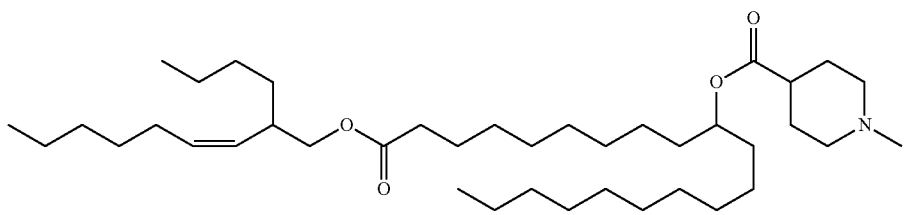
(7)
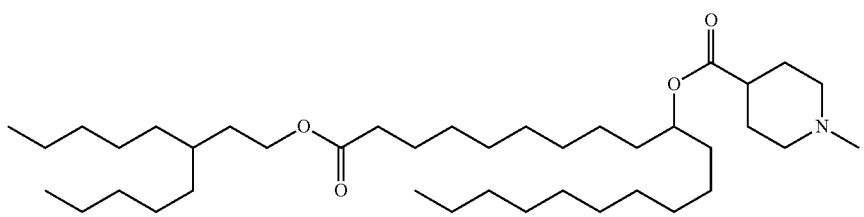
(8)

-continued (9)

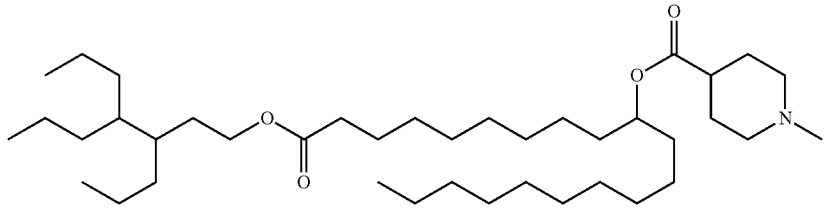

[3] The compound according to [1] or [2] represented by the following Formula (1) or a pharmaceutically acceptable salt thereof.

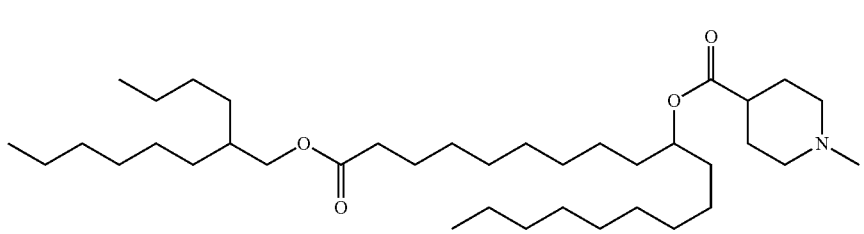

The compound represented by Formula (1) is a cationic lipid.

[4] The compound according to [1] or [2] represented by the following Formula (6) or a pharmaceutically acceptable salt thereof.

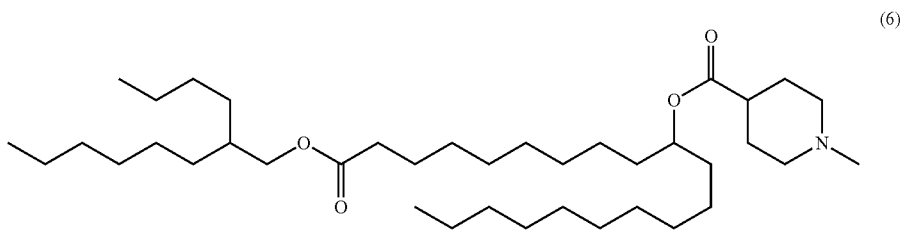 [SMILES: CCCCCCCCCCC(CCCCCCCCC(=O)OCC(CCCC)CCCCCC)OC(=O)C1CCN(C)CC1]

The compound represented by Formula (6) is a cationic lipid.

[5] The compound according to [1] or [2] represented by the following Formula (8) or a pharmaceutically acceptable salt thereof.

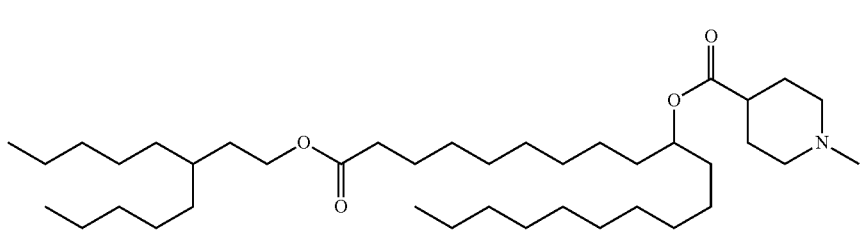

The compound represented by Formula (8) is a cationic lipid.

[6] A lipid complex containing: (I) a compound according to any one of [1] to [5] or a pharmaceutically acceptable salt thereof; and (II) at least one lipid selected from the group consisting of a neutral lipid, a polyethylene glycol-modified lipid, and a sterol.

[7] A composition containing: (I) a compound according to any one of [1] to [5] or a pharmaceutically acceptable salt thereof; (II) at least one lipid selected from the group consisting of a neutral lipid, a polyethylene glycol-modified lipid, and a sterol; and (III) nucleic acid.

[8] A method of producing a composition including: a process of mixing a polar organic solvent-containing aqueous solution which contains (I) a compound according to any one of [1] to [5] or a pharmaceutically acceptable salt thereof, and (II) at least one lipid selected from the group consisting of a neutral lipid, a polyethylene glycol-modified lipid, and a sterol, and an aqueous solution which contains (III) nucleic acid to obtain a mixed solution; and a process of decreasing the content of the polar organic solvent in the mixed solution.

Advantageous Effects of the Invention

According to the cationic lipid of the present invention, it is possible to efficiently release a nucleic acid to the cytoplasm. Therefore, the cationic lipid of the present invention can be applied as a lipid used to deliver a nucleic acid into the cytoplasm.

DESCRIPTION OF EMBODIMENTS

<Cationic Lipid>

Figure 1:
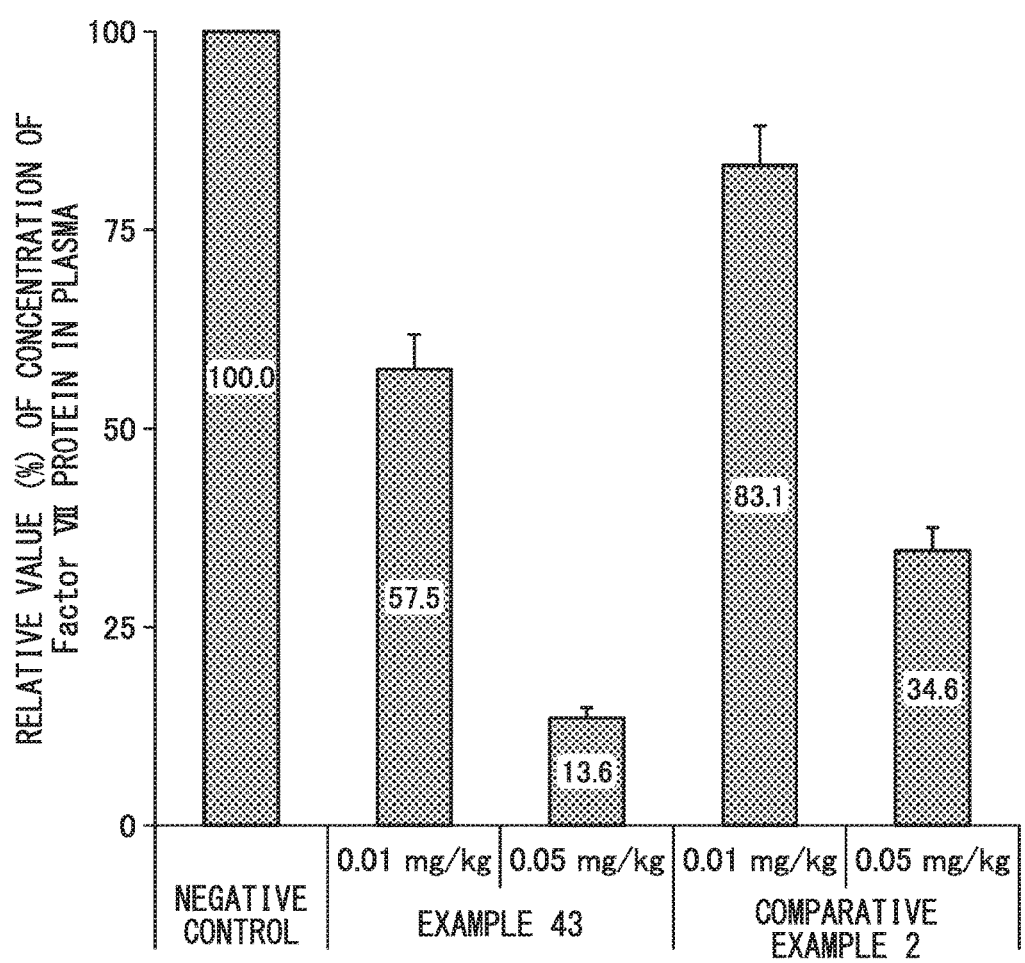
FIG. 1 is a graph showing results of an animal experiment (4).

According to an embodiment, the present invention relates to a compound represented by any of Formulae (1) to (11) or a pharmaceutically acceptable salt thereof and these can be used as a cationic lipid. The cationic lipid may be a hydrate of the salt or a solvate of the salt. In the present specification, the cationic lipid is an amphiphilic molecule which has a lipophilic region containing one or more hydrocarbon groups and a hydrophilic region containing a polar group protonated at a physiological pH. In other words, the cationic lipid of the present invention may be protonated to form a cation. An anion which can be contained in the cationic lipid of the present embodiment by being paired with the cation is not particularly limited as long as the anion is pharmaceutically acceptable, and examples thereof include an inorganic ion such as a chloride ion, a bromide ion, a nitrate ion, a sulfate ion, or a phosphate ion; and an organic acid ion such as an acetate ion, an oxalate ion, a maleate ion, a fumarate ion, a citrate ion, a benzoate ion, or a methanesulfonate ion.

<Method of Producing Cationic Lipid>

A method of producing the cationic lipid of the present invention will be described. The following Formula (12) shows one embodiment of a synthesis scheme of the cationic lipid.

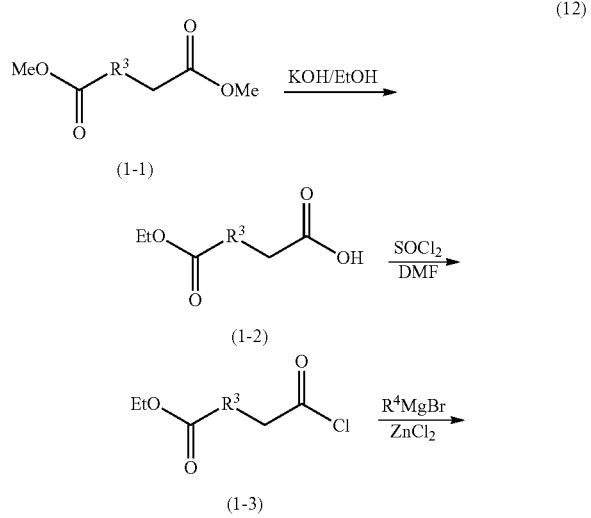

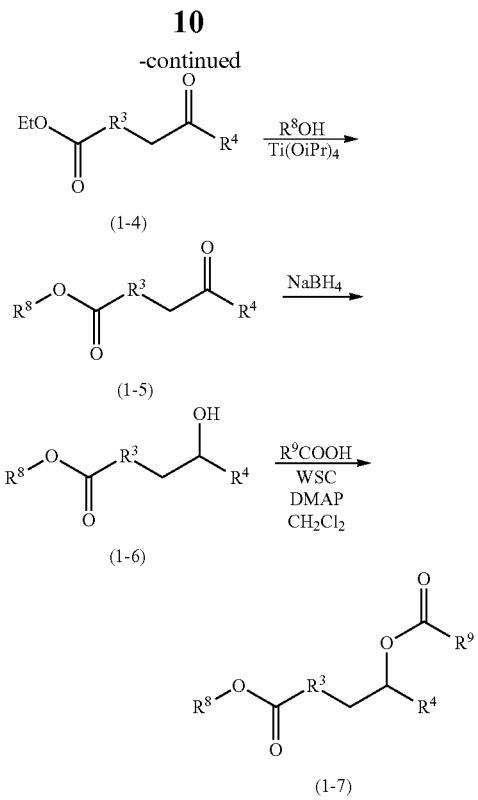

In Formula (12), $R^3$ represents an alkylene group having 4 to 12 carbon atoms, $R^4$ represents an alkyl group having 7 to 12 carbon atoms, $R^8$ represents a structure represented by the following Formula (13), and $R^9$ represents a structure represented by the following Formula (14).

[In Formula (13), $R^1$ represents an alkyl group having 4 to 10 carbon atoms which may have one or more cyclopropanes or cyclobutanes formed by a part of the carbon chain being condensed or an alkenyl group having 4 to 10 carbon atoms, $R^2$ represents a hydrogen atom or an alkyl group having 2 to 8 carbon atoms, and m represents an integer of 0 to 5.]

[In Formula (14), $R^5$, $R^6$, and $R^7$ each independently represents a hydrogen atom or an alkyl group having 1 to 10 carbon atoms and n represents an integer of 0 to 5. $R^5$ and $R^6$ may be bonded to each other to form a monocyclic heterocycle and $R^6$ and $R^7$ may be bonded to each other to form a monocyclic heterocycle.]

In the synthesis scheme of the present embodiment, a cationic lipid (1-7) can be synthesized in the following manner.

First, dialkyl dicarboxylate represented by Formula (1-1) is hydrolyzed to obtain a monoester represented by Formula (1-2). Here, an example in which the alkyl group of the dialkyl dicarboxylate is a methyl group is shown in Formula (1-1), but the alkyl group of dialkyl dicarboxylate is not limited to a methyl group and a suitable alkyl group can be selected.

Next, a compound represented by Formula (1-3) is obtained by forming a compound represented by Formula (1-2) into an acid chloride. Subsequently, a compound represented by Formula (1-4) is obtained by reacting a Grignard reagent with the compound represented by Formula (1-3). Next, a compound represented by Formula (1-6) is obtained by obtaining and reducing a compound represented by Formula (1-5) through a transesterification reaction. Next, the cationic lipid (1-7) can be synthesized by condensing the compound represented by Formula (1-6) with a carboxylic acid.

<Lipid Complex>

The present invention provides a lipid complex containing (I) the cationic lipid described above; and (II) at least one lipid selected from the group consisting of a neutral lipid, a polyethylene glycol-modified lipid, and a sterol. According to one embodiment of the present invention, the lipid complex contains (I) the cationic lipid described above; (II) at least one lipid selected from the group consisting of a neutral lipid, a polyethylene glycol-modified lipid, and a sterol; and (III) nucleic acid. The lipid complex of the present embodiment enables a nucleic acid to be efficiently released to the cytoplasm.

The content of the above-described cationic lipid in the lipid complex of the present embodiment is, for example, in a range of 10% to 100% by mole, for example, in a range of 20% to 90% by mole, and for example, in a range of 40% to 70% by mole based on the total lipids contained in the lipid complex. The cationic lipid can be used alone or in combination of two or more kinds thereof.

Examples of the nucleic acid include siRNA, miRNA, a shRNA expression vector, antisense oligonucleotide, and ribozyme. The nucleic acid may be siRNA or miRNA.

The content of the nucleic acid in the lipid complex of the present embodiment is, for example, in a range of 0.01% to 50% by weight, for example, in a range of 0.1% to 30% by weight, and for example, in a range of 1% to 10% by weight.

The lipid complex of the present embodiment contains, as lipid components, (I) the cationic lipid described above; and (II) at least one lipid selected from the group consisting of a neutral lipid, a polyethylene glycol-modified lipid, and a sterol.

Examples of the neutral lipid include dioleoylphosphatidylethanolamine (DOPE), palmitoyl oleoylphosphatidylcholine (POPC), egg phosphatidylcholine (EPC), dimyristoylphosphatidylcholine (DMPC), dipalmitoylphosphatidylcholine (DPPC), distearoyl phosphatidylcholine (DSPC), diarachidoyl phosphatidylcholine (DAPC), dibehenoyl phosphatidylcholine (DBPC), diligoceroyl phosphatidylcholine (DLPC), dioleoylphosphatidylcholine (DOPC), sphingomyelin, ceramide, dioleoylphosphatidylglycerol (DOPG), dipalmitoylphosphatidylglycerol (DPPG), phosphatidylethanolamine (POPE), and dioleoyl-phosphatidylethanolamine 4-(N-maleimidomethyl)-cyclohexane-1-carboxylate (DOPE-mal). The neutral lipid may be used alone or in combination of two or more kinds thereof.

The content of the neutral lipid in the lipid complex of the present embodiment is, for example, in a range of 0% to 50% by mole, for example, in a range of 0% to 40% by mole, and for example, in a range of 0% to 30% by mole based on the total lipids contained in the lipid complex.

Examples of the polyethylene glycol-modified lipid include PEG2000-DMG (PEG2000-dimyristyl glycerol, PEG2000-DPG (PEG2000-dipalmitoyl glycerol), PEG2000-DSG (PEG2000-distearoyl glycerol), PEG5000-DMG (PEG5000-dimyristyl glycerol, PEG5000-DPG (PEG5000-dipalmitoyl glycerol), PEG5000-DSG (PEG5000-distearoyl glycerol), PEG-cDMA (N-[(methoxy-poly(ethyleneglycol)2000)carbamyl]-1,2-dimyristyloxyl-propyl-3-amine), PEG-C-DOMG (R-3-[(ω-methoxy-poly(ethyleneglycol)2000)carbamoyl])-1,2-dimyristyloxylpropyl-3-amine), polyethylene glycol (PEG)-diacyl glycerol (DAG), PEG-dialkyloxypropyl (DAA), PEG-phospholipid, and PEG-ceramide (Cer).

Examples of the PEG-dialkyloxypropyl include PEG-dilauryloxypropyl, PEG-dimyristyloxypropyl, PEG-dipalmityloxypropyl, and PEG-distearyloxypropyl. The polyethylene glycol-modified lipid may be used alone or in combination of two or more kinds thereof.

The content of the polyethylene glycol-modified lipid in the lipid complex of the present embodiment is, for example, in a range of 0% to 30% by mole, for example, in a range of 0% to 20% by mole, and for example, in a range of 0% to 10% by mole based on the total lipids contained in the lipid complex.

Examples of the sterol include cholesterol, dihydrochloesterol, lanosterol, β-sitosterol, campesterol, stigmasterol, brassicasterol, ergocasterol, fucosterol, and 3β-[N—(N',N'-dimethylaminoethyl)carbamoyl]cholesterol (DC-Chol). The sterol may be used alone or in combination of two or more kinds thereof.

The content of the sterol in the lipid complex of the present embodiment is, for example, in a range of 0% to 90% by mole, for example, in a range of 10% to 80% by mole, and for example, in a range of 20% to 50% by mole based on the total lipids contained in the lipid complex.

The combination of lipid components in the lipid complex of the present embodiment is not particularly limited, and examples thereof include the combination of a cationic lipid, a neutral lipid, and a sterol described above and the combination of a cationic lipid, a neutral lipid, a polyethylene glycol-modified lipid, and a sterol described above.

<Composition>

According to one embodiment, the present invention provides a composition containing (I) the cationic lipid described above; (II) at least one lipid selected from the group consisting of a neutral lipid, a polyethylene glycol-modified lipid, and a sterol, and (III) nucleic acid. The composition of the present embodiment enables a nucleic acid to be efficiently released to the cytoplasm. The composition of the present embodiment may contain the above-described lipid complex, a pharmaceutically acceptable medium, and other additives as necessary. The pharmaceutically acceptable medium and other additives will be described below.

The content of the above-described cationic lipid in the composition of the present embodiment is, for example, in a range of 10% to 100% by mole, for example, in a range of 20% to 90% by mole, and for example, in a range of 40% to 70% by mole based on the total lipids contained in the composition. The cationic lipid may be used alone or in combination of two or more kinds thereof.

Examples of the nucleic acid are the same as those described above. The content of the nucleic acid in the composition of the present embodiment is, for example, in a range of 0.01% to 50% by weight, for example, in a range of 0.1% to 30% by weight, and for example, in a range of 1% to 10% by weight.

The composition of the present embodiment contains, as lipid components, (I) the cationic lipid described above; and (II) at least one lipid selected from the group consisting of a neutral lipid, a polyethylene glycol-modified lipid, and a sterol.

Examples of the neutral lipid are the same as those described above. The content of the neutral lipid in the composition of the present embodiment is, for example, in a range of 0% to 50% by mole, for example, in a range of 0% to 40% by mole, and for example, in a range of 0% to 30% by mole based on the total lipids contained in the composition.

Examples of the polyethylene glycol-modified lipid are the same as those described above. The content of the polyethylene glycol-modified lipid in the composition of the present embodiment is, for example, in a range of 0% to 30% by mole, for example, in a range of 0% to 20% by mole, and for example, in a range of 0% to 10% by mole based on the total lipids contained in the composition.

Examples of the sterol are the same as those described above. The content of the sterol in the composition of the present embodiment is, for example, in a range of 0% to 90% by mole, for example, in a range of 10% to 80% by mole, and for example, in a range of 20% to 50% by mole based on the total lipids contained in the composition.

The combination of lipid components in the composition of the present embodiment is not particularly limited, and examples thereof include the combination of a cationic lipid, a neutral lipid, and a sterol described above and the combination of a cationic lipid, a neutral lipid, a polyethylene glycol-modified lipid, and a sterol described above.

The composition of the present embodiment may contain, as additives other than the above-described components, saccharides such as sucrose, glucose, sorbitol, and lactose; amino acids such as glutamine, glutamic acid, sodium glutamate, and histidine; and salts of acids such as citric acid, phosphoric acid, acetic acid, lactic acid, carbonic acid, and tartaric acid.

The composition of the present embodiment may be formulated as a pharmaceutical composition. As the dosage form of the pharmaceutical composition, an injection agent may be exemplified.

The composition of the present embodiment may be in a powder state formed by removing a solvent through freeze-drying or the like or in a liquid state. In a case where the composition is in the powder state, the composition can be used as an injection agent by being suspended or dissolved in a pharmaceutically acceptable medium before the use. In a case where the composition is in the liquid state, the composition can be used as an injection agent as it is or by being suspended or dissolved in a pharmaceutically acceptable medium.

Examples of the pharmaceutically acceptable medium include sterile water, physiological saline, and an isotonic solution containing an adjuvant such as glucose, D-sorbitol, D-mannose, D-mannitol, or sodium chloride. The composition of the present embodiment may further contain additives such as a solubilizing agent, for example, alcohol such as ethanol, propylene glycol, or polyethylene glycol, a stabilizer, an antioxidant, and a preservative.

The administration of the composition to a patient can be performed by intraarterial injection, intravenous injection, subcutaneous injection, or the like. The amount of composition to be administered varies depending on the administration target, the target organ, the symptoms, and the administration method.

The composition of the present embodiments constitutes a lipid complex formed by a nucleic acid being encapsulated in a fine particle configured of lipids that contain a cationic lipid. The "average particle diameter" of the lipid complex can be calculated by any of methods of obtaining the volume average, the number average, and the Z-average. In the composition of the present embodiment, the average particle diameter (Z-average) of the lipid complex is, for example, in a range of 10 to 1000 nm, for example, in a range of 30 to 500 nm, and for example, in a range of 30 to 200 nm.

From the viewpoints of suppressing non-specific adsorption or an immune reaction, it is preferable that the surface of the composition according to the present embodiment have little charge in an environment in which the pH of the blood is approximately 7.4. Further, from the viewpoint of improving the fusion efficiency with an endosomal membrane, it is preferable that the composition be positively charged in a low pH environment when taken into cells by endocytosis.

<Method of Producing Composition>

In one embodiment, the present invention provides a method of producing a composition, including (a) a process of mixing a polar organic solvent-containing aqueous solution which contains (I) the cationic lipid described above, and (II) at least one lipid selected from the group consisting of a neutral lipid, a polyethylene glycol-modified lipid, and a sterol, and an aqueous solution which contains (III) nucleic acid to obtain a mixed solution; and (b) a process of decreasing the content of the polar organic solvent in the mixed solution. According to the production method of the present embodiment, it is possible to produce a composition capable of efficiently releasing a nucleic acid into the cytoplasm.

The lipid complex formed by a nucleic acid being encapsulated in a fine particle configured of lipids can be formed by an electrostatic interaction between a water-soluble nucleic acid and the above-described cationic lipid and a hydrophobic interaction between lipids. For example, the lipid complex can be formed by changing the solubility of the lipid component containing (I) the cationic lipid described above and (II) at least one lipid selected from the group consisting of a neutral lipid, a polyethylene glycol-modified lipid, and a sterol with respect to a polar organic solvent-containing aqueous solution. Examples of the polar organic solvent include alcohol such as ethanol.

First, in the process (a), a mixed solution is obtained by mixing the polar organic solvent-containing aqueous solution in which (I) the cationic lipid described above, and (II) at least one lipid selected from the group consisting of a neutral lipid, a polyethylene glycol-modified lipid, and a sterol are dissolved, and the aqueous solution which contains (III) nucleic acid. The concentration of the polar organic solvent in the polar organic solvent-containing aqueous solution is not particularly limited as long as the conditions in which the lipid molecules are dissolved even after the polar organic solvent is mixed with the aqueous solution containing a nucleic acid are satisfied.

Next, in the process (b), the content of the polar organic solvent is decreased by adding water or the like to the above-described mixed solution. In this manner, the lipid complex can be formed. In order to efficiently form the lipid complex, it is preferable that the content of the polar organic solvent be drastically decreased.

According to the method of producing a composition of the present embodiment, it is possible to obtain a lipid complex formed by a nucleic acid being efficiently encapsulated in a fine particle.

In a case where the nucleic acid encapsulated by a composition is nucleic acid medicine, the composition can be utilized as a pharmaceutical composition.

EXAMPLES

Hereinafter, the present invention will be described in more detail with reference to examples, but the present invention is not limited to these examples. Further, the compound names in the examples are named using software ("ChemDraw Ultra ver. 12.0" (trade name), manufactured by PerkinElmer, Inc.).

The abbreviations used in the examples are conventional abbreviations known to those skilled in the art. Some of the abbreviations are shown below.

DMF: N,N-dimethylformamide
TFA: triflouroacetic acid
WSC: 1-ethyl-3-(3-dimethylaminopropyl)carbodiimide hydrochloride
DMAP: N,N-dimethyl-4-aminopyridine
THF: tetrahydrofuran
LC-MS: liquid chromatography-mass spectrometry
ESI-MS: electrospray ionization mass spectrometry The chemical shifts of the proton nuclear magnetic resonance spectra are recorded in δ units (ppm) with respect to tetramethylsilane. The abbreviations of the pattern are as follows.

s: singlet, d: doublet, t: triplet, q: quartet, dd: double doublet, ddd: double double doublet, dt: double triplet, tt: triple triplet, m: multiplet Synthesis of Cationic Lipid Example 1

Synthesis of 1-((2-hexylcyclopropyl)methoxy)-1-oxononadecane-10-yl-1-methylpiperidine-4-carboxylate (hereinafter, also referred to as "YS-102")

Hereinafter, the synthesis scheme of YS-102 is shown.

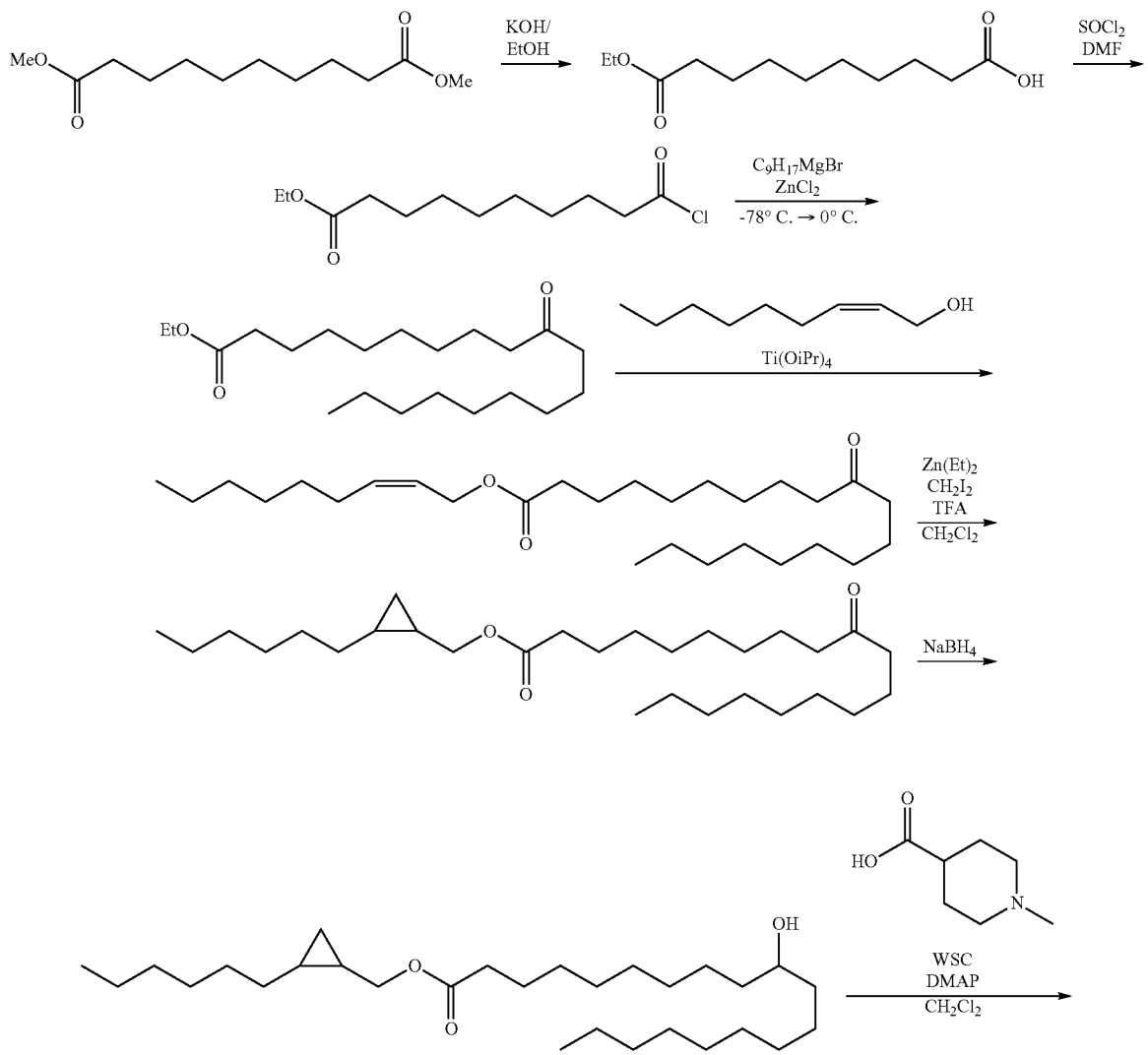

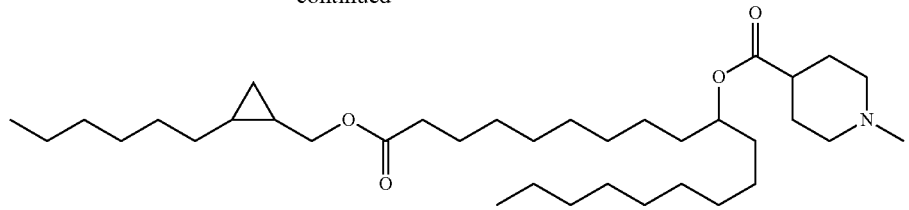

(First Process: Hydrolysis)

A solution obtained by dissolving dimethyl sebacate (200 g, 868.4 mmol) in ethanol (868 mL) was cooled to 0° C. A solution of potassium hydroxide (48.73 g, 868.4 mmol) in ethanol (300 mL) was added dropwise to the solution and the solution was stirred at 0° C. for 12 hours after the dropwise addition. After the reaction was finished, ethyl acetate and water were added thereto and an unreacted substance was removed by being extracted to an organic layer. The water layer was acidified using hydrochloric acid, and ethyl acetate was added thereto so that a target object was extracted. The organic layer was washed with water and saline and then concentrated. A first process product monoester (150.3 g, 652.6 mmol, 75%) was used for the next step without performing purification.

(Second Process: Formation of Acid Chloride)

Thionyl chloride (41.3 g, 346.8 mmol) was added dropwise to a suspension of the first process product monoester (50.0 g, 231.2 mmol) and a catalytic amount of DMF (23 mL). After the reaction was finished, the thionyl chloride was distilled off under reduced pressure, distilled, and then purified, thereby obtaining a second process product (25.8 g, 109.9 mmol, 48%).

(Third Process: Reaction with Grignard Reagent)

Zinc chloride (2.7 g, 20.1 mmol) was dissolved in THF (61 mL) and the solution was cooled to −78° C. 1 M nonyl magnesium bromide (40.2 mL, 40.2 mmol) was added dropwise to the solution at −78° C. in a nitrogen atmosphere. The solution was heated to 0° C. after the dropwise addition and stirred at 0° C. for 30 minutes, tetrakis triphenylphosphine palladium (0.58 mg, 0.5 mmol) was put into the solution, and then the second process product was added dropwise thereto (5.0 g, 20.1 mmol). After the solution was further stirred at 0° C. for 1 hour, 1 M hydrochloric acid aqueous solution was added thereto and then the solution was quenched. A precipitate was separated by filtration from the reaction solution, the filtrate was extracted using ethyl acetate, and the organic layer was washed with water and saline and then dried over anhydrous magnesium sulfate. A drying agent was removed by filtration, and the filtrate was concentrated under reduced pressure. The resultant was purified by silica gel column chromatography, thereby obtaining a third process product (5.0 g, 14.7 mmol, 73%).

(Fourth Process: Transesterification)

An outer bath was heated to 110° C. while a mixed solution of the third process product (2.0 g, 5.9 mmol), 2-nonenol (4.2 g, 29.4 mmol), and titanium tetrapropoxide (0.2 g, 0.6 mmol) was stirred. The mixed solution was continuously stirred while the generated distillate was removed and then cooled after the time point at which the distillate was not found any longer as the end point of the reaction, water was added thereto, and then the solution was quenched. The reaction solution was extracted using ethyl acetate, washed with water and saline, and then dried over anhydrous magnesium sulfate. A drying agent was removed by filtration, and the filtrate was concentrated under reduced pressure. The resultant was purified by silica gel column chromatography, thereby obtaining a fourth process product (2.6 g, 5.8 mmol, 99%).

(Fifth Process: Cyclopropanation)

Diethyl zinc (8.3 mL, 8.3 mmol) was dissolved in dichloromethane (15 mL) and the solution was cooled to 0° C. Trifluoromethanesulfonic acid (0.9 g, 8.3 mmol) was added dropwise to the solution, diiodomethane (2.2 g, 8.3 mmol) was added dropwise thereto, and then the solution was stirred at 0° C. for 1 hour. The solution of the fourth process product (1.2 g, 2.8 mmol) in dichloromethane (5 mL) was added dropwise to the solution and the solution was heated to room temperature. The reaction was confirmed using TLC and the solution was quenched using water after the time point at which the raw material disappeared as the end point. The precipitated solid was separated by filtration, and the filtrate was extracted using ethyl acetate, washed with water and saline, and then dried over anhydrous magnesium sulfate. A drying agent was removed by filtration, and the filtrate was concentrated under reduced pressure. The resultant was purified by silica gel column chromatography, thereby obtaining a fourth process product (1.2 g, 2.7 mmol, 99%).

(Sixth Process: Reduction)

Sodium borohydride (0.08 g, 2.2 mmol) was added to a solution obtained by dissolving the fifth process product (1.0 g, 2.2 mmol) in ethanol (22 mL) and the reaction was allowed to proceed for 10 minutes. After the reaction was finished, the solution was quenched using 1 N hydrochloric acid. The reaction solution was extracted using ethyl acetate and washed with water and saline, and the organic layer was concentrated under reduced pressure. The resultant was purified by silica gel column chromatography, thereby obtaining a sixth process product (0.3 g, 0.7 mmol, 30%).

(Seventh Process: Condensation)

WSC (0.7 g, 3.7 mmol), dimethylaminopyridine (0.04 g, 0.4 mmol), and 1-methylpiperidine-4-carboxylic acid (0.5 g, 3.7 mmol) were added to a solution obtained by dissolving the sixth process product (0.8 g, 1.8 mmol) in methylene chloride (7 mL). After the solution was stirred at room temperature until the next day, water was added thereto, and the organic layer was subjected to liquid separation. The organic layer was washed with water five times, further washed with a 1 N sodium hydroxide aqueous solution once, and dried over anhydrous magnesium sulfate. A drying agent was removed by filtration, and the filtrate was concentrated under reduced pressure. The resultant was purified by silica gel column chromatography, thereby obtaining YS-102 (0.12 g, 0.2 mmol, 12%) represented by the following Formula (15).

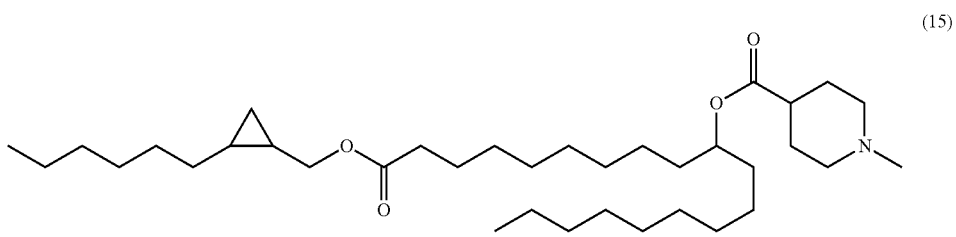 [SMILES: CCCCCCCCCC(CCCCCCCCC(=O)OCC1CC1CCCCCC)OC(=O)C1CCN(C)CC1]

(15)

The obtained compound was confirmed by HPLC-LC/MS under the following conditions. Column: YMC-TriartC18, 150-4.6 mm, 5 μm, eluent: MeOH (uniform solvent), flow rate: 1.0 mL/min, runtime: 15 minutes, column temperature: 45° C., detection: UV (215 nm), electrospray ionization mass spectrometry (ESI-MS).

HPLC-LC/MS, Rt 6.24 minutes, ESI-MS (M+H) cacld 577.5, found 578.6, $^1$H NMR (400 MHz, CDCl$_3$) δ7 (1H, q), 2.82 (2H, d), 2.27 (4H, m), 2.04 (1H, m), 1.91 (1H, m), 1.82 (2H, m), 1.61 (2H, m), 1.50 (4H, m), 1.36 (5H, m), 1.25 (24H, m), 0.88 (6H, m)

Example 2

Synthesis of (Z)-1-(non-2-en-1-yloxy)-1-oxononadecane-10-yl-1-methylpiperidine-4-carboxylate (hereinafter, also referred to as "YS-101")

YS-101 represented by the following Formula (16) was synthesized in the same manner as in Example 1 except that the fifth process was not performed.

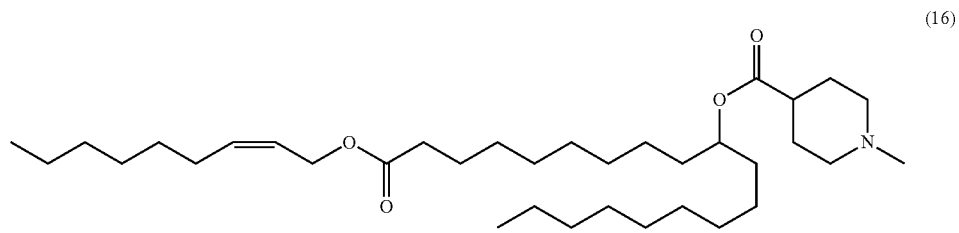 [SMILES: CCCCCC/C=C\COC(=O)CCCCCCCCC(CCCCCCCCC)OC(=O)C1CCN(C)CC1]

(16)

HPLC-LC/MS, Rt 5.51 minutes, ESI-MS(M+H) cacld 563.5, found 564.5, $^1$H NMR (400 MHz, CDCl$_3$) δ5.32 (2H, m), 4.87 (1H, q), 4.11 (1H, dd), 4.05 (2H, t), 2.82 (2H, d), 2.27 (7H, m), 2.04 (8H, m), 1.89 (2H, m), 1.79 (2H, m), 1.61 (4H, m), 1.49 (4H, m), 1.36 (5H, m), 1.25 (30H, m), 0.95 (3H, m), 0.88 (3H, m)

Example 3

Synthesis of 1-oxo-1-(undecane-5-yloxy)nonadecane-10-yl-1-methylpiperidine-4-carboxylate (hereinafter, also referred to as "YS-103")

YS-103 represented by the following Formula (2) was synthesized in the same manner as in Example 1 except that 2-butyloctane-1-ol was reacted in place of 2-nonenol in the fourth process and the fifth process was not performed.

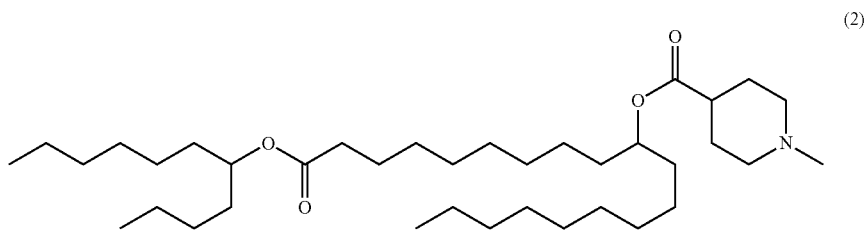 [SMILES: CCCCCCCCCC(CCCCCCCCC(=O)OC(CCCC)CCCCCC)OC(=O)C1CCN(C)CC1]

(2)

HPLC-LC/MS, Rt 7.52 minutes, ESI-MS (M+H) cacld 593.5, found 594.6, $^1$H NMR (400 MHz, CDCl$_3$) δ4.86 (1H, q), 4.06 (2H, t), 2.82 (2H, d), 2.27 (7H, m), 1.99 (2H, m), 1.88 (2H, m), 1.79 (2H, m), 1.60 (4H, m), 1.49 (4H, m), 1.38 (7H, m), 1.25 (30H, m), 0.97 (3H, m), 0.88 (3H, m), 0.64 (2H, m), 0.59 (1H, m), −0.33 (1H, dd)

Example 4

Synthesis of 1-((2-butyloctyl)oxy)-1-oxononadecane-10-yl-1-methylpiperidine-4-carboxylate (hereinafter, also referred to as "YS-119")

Hereinafter, the synthesis scheme of YS-119 is shown.

(First to Third Processes)

The first to third processes were the same as those for the synthesis of YS-102 described above.

(Fourth Process: Transesterification)

An outer bath was heated to 110° C. while a mixed solution of the third process product (4.1 g, 12.0 mmol), 2-butyloctane-1-ol (6.73 g, 36.12 mmol), and titanium tetrapropoxide (0.34 g, 1.2 mmol) was stirred. The mixed solution was continuously stirred while the generated distillate was removed and then cooled after the time point at which the distillate was not found any longer as the end point of the reaction, water was added thereto, and then the solution was quenched. The reaction solution was extracted using ethyl acetate, washed with water and saline, and then dried over anhydrous magnesium sulfate. A drying agent was removed by filtration, and the filtrate was concentrated under reduced pressure. The resultant was purified by silica gel column chromatography, thereby obtaining a fourth process product (4.5 g, 9.4 mmol, 78%).

(Fifth Process: Reduction)

Sodium borohydride (1.8 g, 46.8 mmol) was added to a solution obtained by dissolving the fourth process product (4.5 g, 9.4 mmol) in THF (18.7 mL) and methanol (18.7 mL) and the reaction was allowed to proceed for 1 hour. After the reaction was finished, the solution was quenched using 1 N hydrochloric acid. The reaction solution was extracted using ethyl acetate and washed with water and saline, and the organic layer was concentrated under reduced pressure. The resultant was purified by silica gel column chromatography, thereby obtaining a fifth process product (3.1 g, 6.42 mmol, 69%).

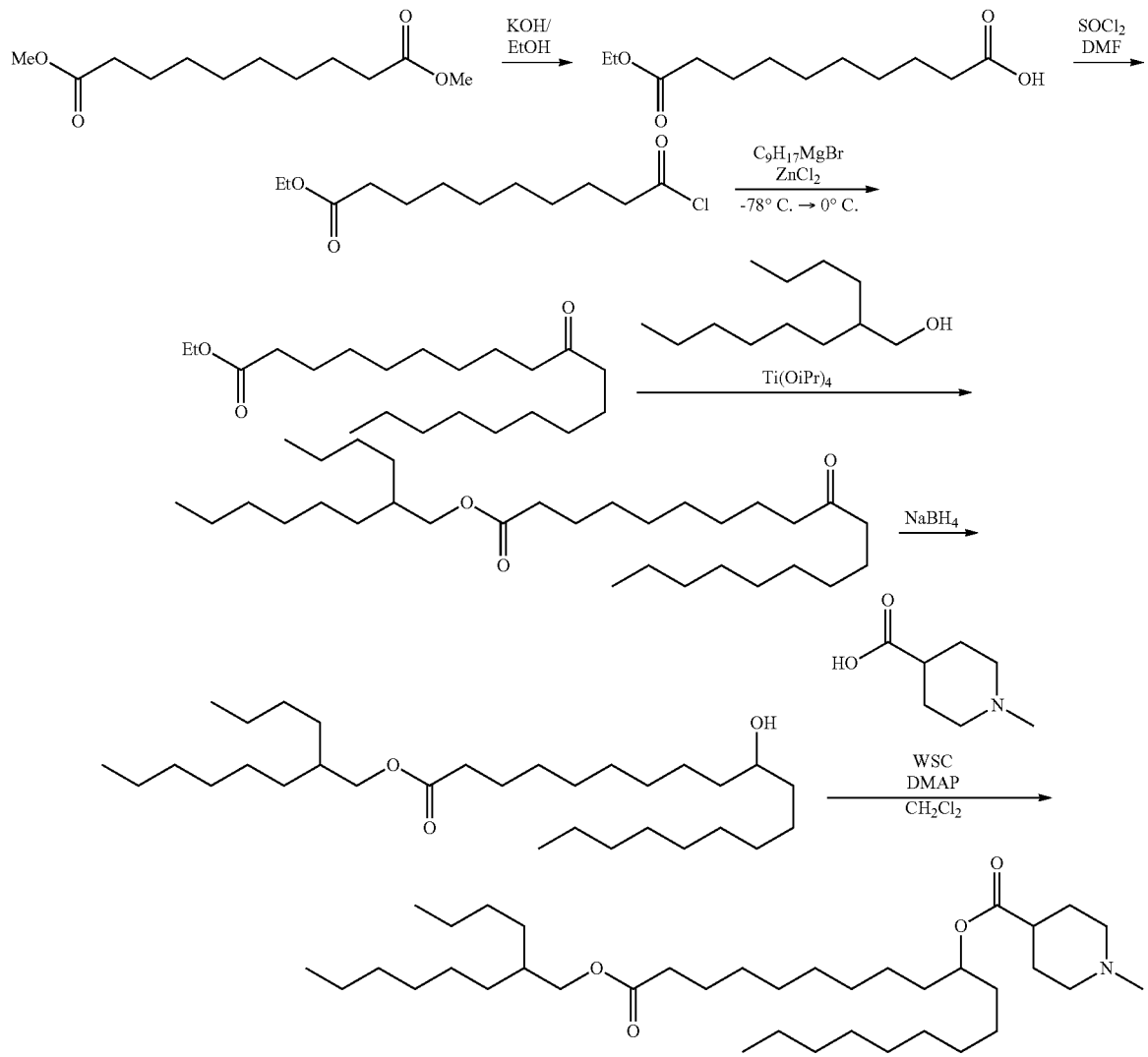

(Sixth Process: Condensation)

WSC (1.59 g, 8.28 mmol), dimethylaminopyridine (0.04 g, 0.4 mmol), and 1-methylpiperidine-4-carboxylic acid (L19 g, 8.28 mmol) were added to a solution obtained by dissolving the fifth process product (2.0 g, 4.14 mmol) in methylene chloride (8.28 mL). After the solution was stirred at room temperature until the next day, water was added thereto, and the organic layer was subjected to liquid separation. The organic layer was washed with water five times, further washed with a 1 N sodium hydroxide aqueous solution once, and dried over anhydrous magnesium sulfate. A drying agent was removed by filtration, and the filtrate was concentrated under reduced pressure. The resultant was purified by silica gel column chromatography, thereby obtaining YS-119 (1.9 g, 3.1 mmol, 74%) represented by Formula (1).

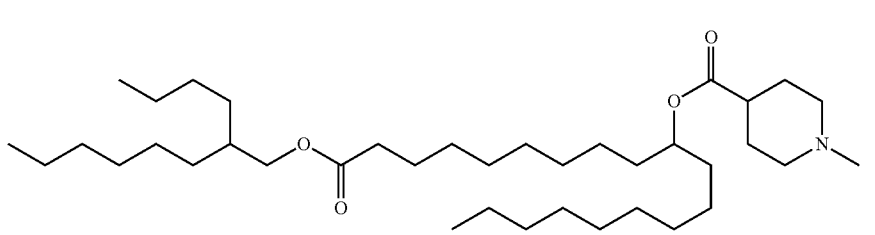

(1)

HPLC-LC/MS, Rt 8.01 minutes, ESI-MS (M+H) cacld 607.6, found 608.6, NMR (400 MHz, CDCl$_3$) δ4.87 (1H, q), 3.96 (2H, d), 2.81 (2H, d), 2.27 (6H, m), 1.98 (2H, m), 1.91 (2H, m), 1.82 (2H, m), 1.61 (4H, m), 1.49 (4H, m), 1.20 (46H, m), 0.86 (9H, m)

Example 5

Synthesis of 1-oxo-1-(undecane-5-yloxy)pentadecane-6-yl-1-methylpiperidine 4-carboxylate (hereinafter, also referred to as "YS-111")

YS-111 represented by the following Formula (17) was synthesized in the same manner as in Example 4 except that dimethyl adipate was reacted in place of dimethyl sebacate in the first process and undecane-5-ol was reacted in place of 2-butyloctane-1-ol in the fourth process.

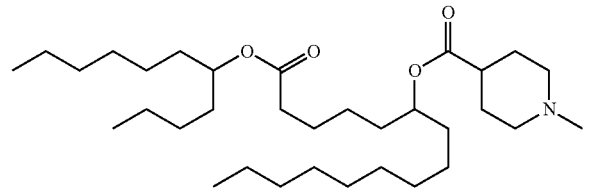

(17)

HPLC-LC/MS, Rt 5.35 minutes, ESI-MS (M+H) cacld 537.5, found 538.5, $^1$H NMR (400 MHz, CDCl$_3$) δ4.87 (2H, q), 2.81 (2H, d), 2.27 (6H, m), 1.98 (2H, m), 1.91 (2H, m), 1.82 (2H, m), 1.62-1.50 (10H, m), 1.24 (28H, m), 0.87 (9H, m)

Example 6

Synthesis of 1-oxo-1-(undecane-5-yloxy)heptadecane-8-yl-1-methylpiperidine 4-carboxylate (hereinafter, also referred to as "YS-112")

YS-112 represented by the following Formula (4) was synthesized in the same manner as in Example 4 except that dimethyl suberate was reacted in place of dimethyl sebacate in the first process and undecane-5-ol was reacted in place of 2-butyloctane-1-ol in the fourth process.

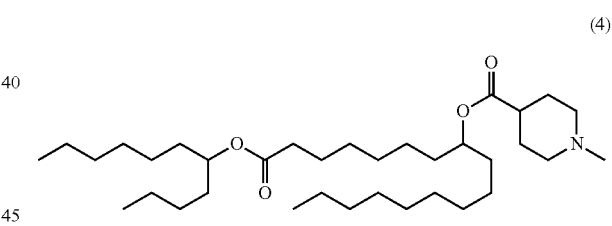

(4)

HPLC-LC/MS, Rt 6.05 minutes, ESI-MS (M+H) cacld 565.5, found 566.5, $^1$H NMR (400 MHz, CDCl$_3$) δ4.87 (2H, q), 2.81 (2H, d), 2.27 (6H, m), 1.98 (2H, m), 1.91 (2H, m), 1.82 (2H, m), 1.62-1.50 (10H, m), 1.24 (32H, m), 0.87 (9H, m)

Example 7

Synthesis of 21-oxo-21-(undecane-5-yloxy)henicosane-10-yl-1-methylpiperidine 4-carboxylate (hereinafter, also referred to as "YS-113")

YS-113 represented by the following Formula (5) was synthesized in the same manner as in Example 4 except that dimethyl dodecanedioate was reacted in place of dimethyl sebacate in the first process and undecane-5-ol was reacted in place of 2-butyloctane-1-ol in the fourth process.

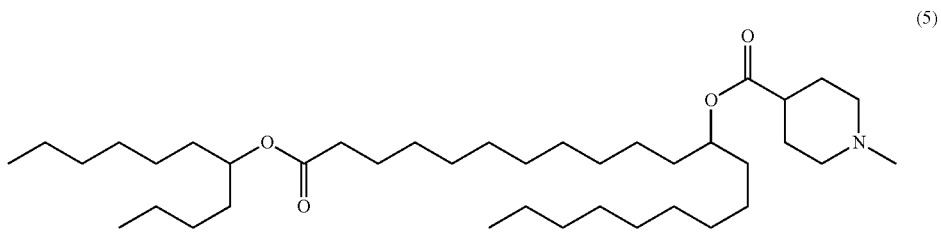 [SMILES: CCCCCCCCCC(CCCCCCCCCCC(=O)OC(CCCC)CCCCCC)OC(=O)C1CCN(C)CC1]

(5)

HPLC-LC/MS, Rt 8.95 minutes, ESI-MS (M+H) cacld 621.6, found 622.6, $^1$H NMR (400 MHz, CDCl$_3$) δ4.87 (2H, q), 2.81 (2H, d), 2.27 (6H, m), 1.98 (2H, m), 1.91 (2H, m), 1.82 (2H, m), 1.62-1.50 (10H, m), 1.24 (40H, m), 0.87 (9H, m)

Example 8

Synthesis of 23-oxo-23-(undecane-5-yloxy)tricosane-10-yl-1-methylpiperidine 4-carboxylate (hereinafter, also referred to as "YS-114")

YS-114 represented by the following Formula (18) was synthesized in the same manner as in Example 4 except that dimethyl tetradecanedioate was reacted in place of dimethyl sebacate in the first process and undecane-5-ol was reacted in place of 2-butyloctane-1-ol in the fourth process.

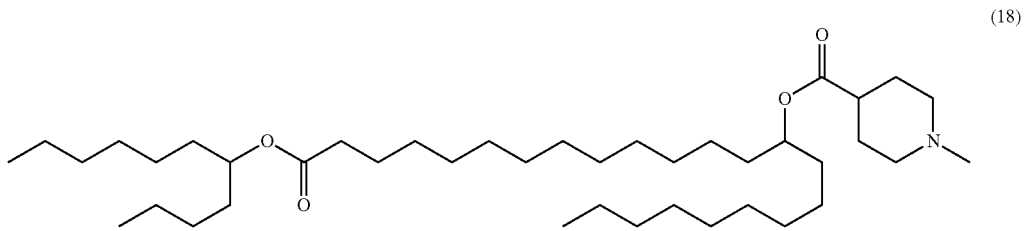 [SMILES: CCCCCCCCCC(CCCCCCCCCCCCC(=O)OC(CCCC)CCCCCC)OC(=O)C1CCN(C)CC1]

(18)

HPLC-LC/MS, Rt 11.1 minutes, ESI-MS (M+H) cacld 649.6, found 650.6, $^1$H NMR (400 MHz, CDCl$_3$) δ4.87 (2H, q), 2.81 (2H, d), 2.27 (6H, m), 1.98 (2H, m), 1.91 (2H, m), 1.82 (2H, m), 1.62-1.50 (10H, m), 1.24 (44H, m), 0.87 (9H, m)

Example 9

Synthesis of 1-((2-butyloctyl)oxy)-1-oxoheptadecane-8-yl-1-methylpiperidine-4-carboxylate (hereinafter, also referred to as "YS-115")

YS-115 represented by the following Formula (19) was synthesized in the same manner as in Example 4 except that dimethyl suberate was reacted in place of dimethyl sebacate in the first process.

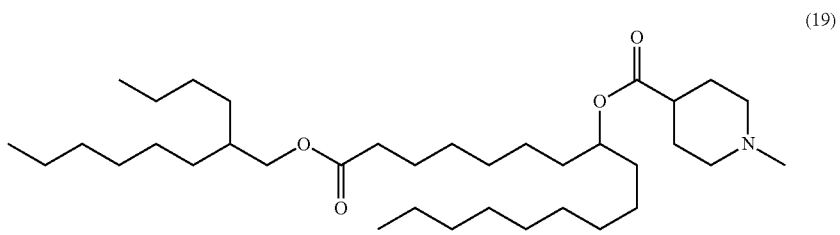 [SMILES: CCCCCCCCCC(CCCCCCC(=O)OCC(CCCC)CCCCCC)OC(=O)C1CCN(C)CC1]

(19)

HPLC-LC/MS, Rt 6.72 minutes, ESI-MS (M+H) cacld 579.5, found 580.7, $^1$H NMR (400 MHz, CDCl$_3$) δ4.87 (2H, q), 3.96 (2H, d), 2.81 (2H, d), 2.27 (6H, m), 1.98 (2H, m), 1.91 (2H, m), 1.82 (2H, m), 1.62-1.50 (10H, m), 1.24 (32H, m), 0.87 (9H, m)

Example 10

Synthesis of 21-((2-butyloctyl)oxy)-21-oxohenicosane-10-yl-1-methylpiperidine-4-carboxylate (hereinafter, also referred to as "YS-116")

YS-116 represented by the following Formula (20) was synthesized in the same manner as in Example 4 except that dimethyl suberate was reacted in place of dimethyl sebacate in the first process.

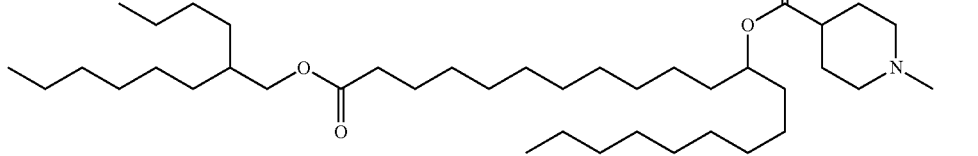
(20)

HPLC-LC/MS, Rt 10.0 minutes, ESI-MS (M+H) cacld 635.6, found 636.7, $^1$H NMR (400 MHz, CDCl$_3$) δ4.87 (2H, q), 3.96 (2H, d), 2.81 (2H, d), 2.27 (6H, m), 1.98 (2H, m), 1.91 (2H, m), 1.82 (2H, m), 1.62-1.50 (10H, m), 1.24 (40H, m), 0.87 (9H, m)

Example 11

Synthesis of 1-(octane-3-yloxy)-1-oxoheptadecane-8-yl-1-methylpiperidine-4-carboxylate (hereinafter, also referred to as "YS-117")

YS-117 represented by the following Formula (21) was synthesized in the same manner as in Example 4 except that dimethyl suberate was reacted in place of dimethyl sebacate in the first process and octane-3-ol was reacted in place of 2-butyloctane-1-ol in the fourth process.

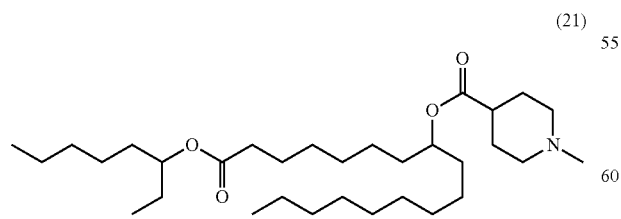
(21)

HPLC-LC/MS, Rt 4.71 minutes, ESI-MS (M+H) cacld 523.5, found 524.6, $^1$H NMR (400 MHz, CDCl$_3$) δ4.87 (1H, q), 4.80 (1H, q), 2.82 (2H, d), 2.27 (6H, m), 1.98 (2H, m), 1.91 (2H, m), 1.82 (2H, m), 1.62-1.29 (10H, m), 1.24 (26H, m), 0.87 (9H, m)

Example 12

Synthesis of 1-((S)octane-3-yloxy)-1-oxoheptadecane-8-yl-1-methylpiperidine-4-carboxylate (hereinafter, also referred to as "YS-117S")

YS-117S represented by the following Formula (22) was synthesized in the same manner as in Example 4 except that dimethyl suberate was reacted in place of dimethyl sebacate in the first process and (S)-octane-3-ol was reacted in place of 2-butyloctane-1-ol in the fourth process.

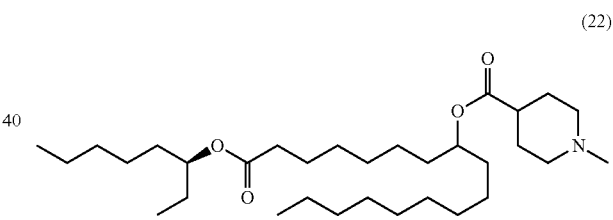
(22)

HPLC-LC/MS, Rt 4.70 minutes, ESI-MS (M+H) cacld 523.5, found 524.6, $^1$H NMR (400 MHz, CDCl$_3$) δ4.87 (1H, q), 4.80 (1H, q), 2.82 (2H, d), 2.27 (6H, m), 1.98 (2H, m), 1.91 (2H, m), 1.82 (2H, m), 1.62-1.29 (10H, m), 1.24 (26H, m), 0.86 (9H, m)

Example 13

Synthesis of 21-(octane-3-yloxy)-21-oxohenlcosane-10-yl-1-methylpiperidine-4-carboxylate (hereinafter, also referred to as "YS-118")

YS-118 represented by the following Formula (3) was synthesized in the same manner as in Example 4 except that dimethyl dodecanedioate was reacted in place of dimethyl sebacate in the first process and octane-3-ol was reacted in place of 2-butyloctane-1-ol in the fourth process.

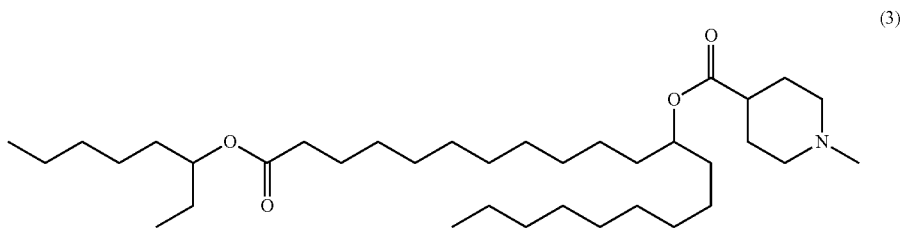 [SMILES: CCCCCCCCCC(CCCCCCCCCCC(=O)OC(CC)CCCCC)OC(=O)C1CCN(C)CC1]

HPLC-LC/MS, Rt 6.55 minutes, ESI-MS (M+H) cacld 579.5, found 580.6, $^1$H NMR (400 MHz, CDCl$_3$) δ4.87 (1H, q), 4.80 (1H, q), 2.82 (2H, d), 2.27 (6H, m), 1.98 (2H, m), 1.91 (2H, m), 1.82 (2H, m), 1.62-1.29 (10H, m), 1.24 (30H, m), 0.86 (9H, m)

Example 14

Synthesis of 21-((S)-octane-3-yloxy)-21-oxohenicosane-10-yl-1-methylpiperidine-4-carboxylate (hereinafter, also referred to as "YS-118S")

YS-118S represented by the following Formula (23) was synthesized in the same manner as in Example 4 except that dimethyl dodecanedioate was reacted in place of dimethyl sebacate in the first process and (S)-octane-3-ol was reacted in place of 2-butyloctane-1-ol in the fourth process.

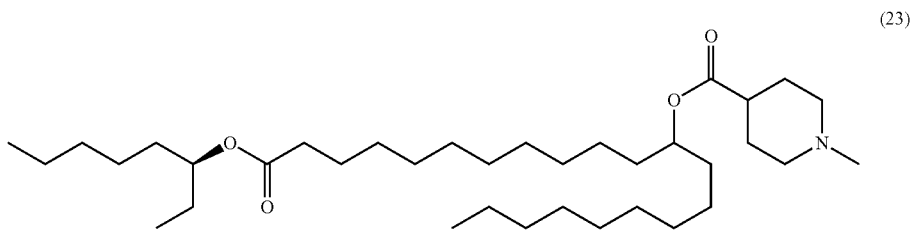 [SMILES: CCCCCCCCCC(CCCCCCCCCCC(=O)O[C@@H](CC)CCCCC)OC(=O)C1CCN(C)CC1]

HPLC-LC/MS, Rt 6.54 minutes, ESI-MS (M+H) cacld 579.5, found 580.6, $^1$H NMR (400 MHz, CDCl$_3$) δ4.87 (1H, q), 4.80 (1H, q), 2.82 (2H, d), 2.27 (6H, m), 1.98 (2H, m), 1.91 (2H, m), 1.82 (2H, m), 1.62-1.29 (10H, m), 1.24 (30H, m), 0.86 (9H, m)

Example 15

Synthesis of 1-((2-butyloctyl)oxy)-1-oxoicosane-10-yl-1-methylpiperidine-4-carboxylate (hereinafter, also referred to as "YS-120")

YS-120 represented by the following Formula (6) was synthesized in the same manner as in Example 4 except that decanyl magnesium bromide was reacted in place of nonyl magnesium bromide in the third process.

HPLC-LC/MS, Rt 8.70 minutes, ESI-MS (M+H) cacld 621.6, found 622.7, $^1$H NMR (400 MHz, CDCl$_3$) δ4.86 (1H, ddd), 3.96 (2H, d), 2.81 (2H, d), 2.27 (6H, m), 2.03 (2H, m), 1.98 (1H, d), 1.90 (1H, m), 1.78 (4H, m), 1.61 (4H, m), 1.49 (4H, m), 1.27-1.21 (41H, m), 0.87 (9H, m)

As described below, when a lipid complex is formed by the compound represented by Formula (6), an increase in particle diameter of the lipid complex in a case of being stored for a certain period is suppressed so that the stability is high.

Example 16

Synthesis of 1-((2-butyloctyl)oxy)-1-oxoicosane-10-yl-1-methylpiperidine-4-carboxylate ("YS-120")

Hereinafter, another synthesis scheme of YS-120 is shown.

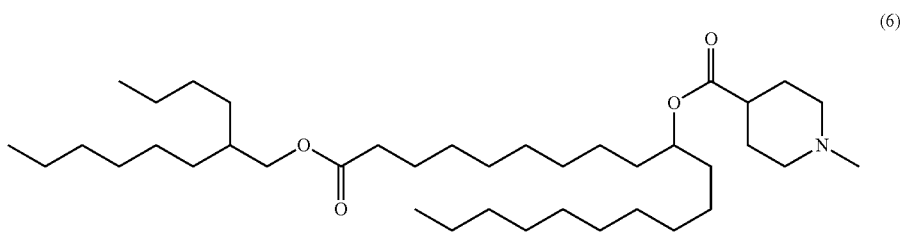 [SMILES: CCCCCCCCCCC(CCCCCCCCC(=O)OCC(CCCC)CCCCCC)OC(=O)C1CCN(C)CC1]

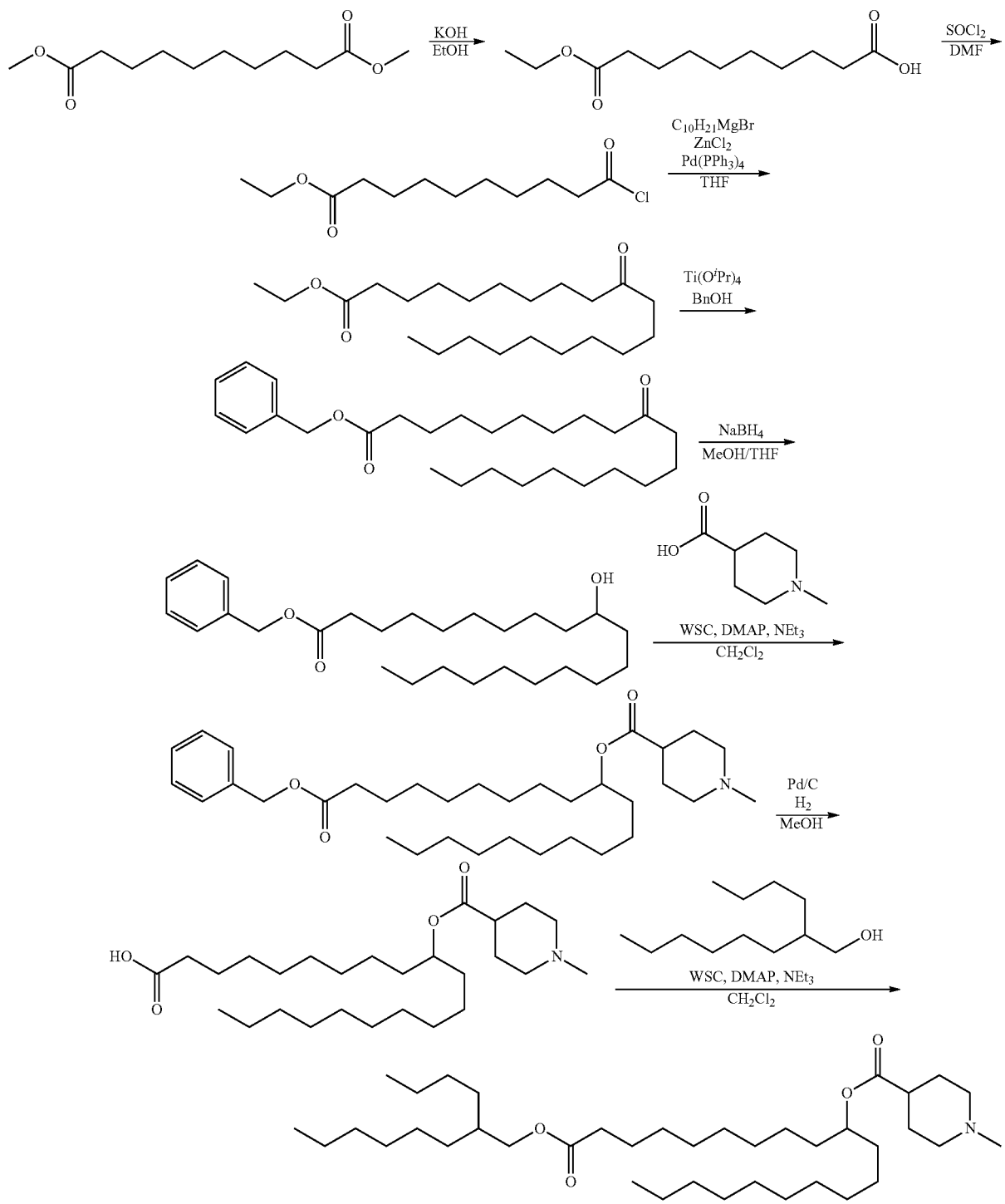

YS-120

(First to Third Processes)

The first to third processes were the same as those for the synthesis of YS-102 described above.

(Fourth Process: Transesterification)

An outer bath was heated to 130° C. while a mixed solution of the third process product (150.0 g, 440.5 mmol), benzyl alcohol (142.9 g, 1321.4 mmol), and titanium tetrapropoxide (12.5 g, 44.5 mmol) was stirred. The mixed solution was continuously stirred while the generated distillate was removed and then cooled after the time point at which the distillate was not found any longer as the end point of the reaction, water was added thereto, and then the solution was quenched. The reaction solution was extracted using ethyl acetate, washed with water and saline, and then dried over anhydrous magnesium sulfate. A drying agent was removed by filtration, and the filtrate was concentrated under reduced pressure. The resultant was purified by silica gel column chromatography, thereby obtaining a fourth process product (146.2 g, 350.9 mmol).

(Fifth Process: Reduction)

Sodium borohydride (10.9 g, 288.0 mmol) was added to a solution obtained by dissolving the fourth process product (100.0 g, 240.0 mmol) in THF (480.0 mL) and methanol (480.0 mL) and the reaction was allowed to proceed for 10 minutes. After the reaction was finished, the solution was quenched using 1 N hydrochloric acid. The reaction solution was extracted using ethyl acetate and washed with water and saline, and the organic layer was concentrated under reduced pressure. The resultant was purified by silica gel column chromatography, thereby obtaining a fifth process product (70.0 g, 167.2 mmol).

(Sixth Process: Condensation)

WSC (45.8 g, 238.9 mmol), dimethylaminopyridine (2.92 g, 23.9 mmol), and 1-methylpiperidine-4-carboxylic acid (34.2 g, 238.9 mmol) were added to a solution obtained by dissolving the fifth process product (50.0 g, 119.4 mmol) in THF (480.0 mL). After the solution was stirred at room temperature until the next day, water was added thereto, and the organic layer was subjected to liquid separation. The organic layer was washed with water five times, further washed with a 1 N sodium hydroxide aqueous solution once, and dried over anhydrous magnesium sulfate. A drying agent was removed by filtration, and the filtrate was concentrated under reduced pressure. The resultant was purified by silica gel column chromatography, thereby obtaining a sixth process product (37.2 g, 68.4 mmol).

(Seventh Process: Catalytic Reduction)

The sixth process product (37.2 g, 68.4 mmol) and palladium/carbon (4.9 mL) were suspended in ethyl acetate (136.8 mL), and the solution was stirred overnight in a hydrogen atmosphere. The reaction solution was separated by filtration and concentrated by removing palladium/carbon. The resultant was purified by silica gel chromatography, thereby obtaining a seventh process product (26.8 g, 59.1 mmol).

(Eighth Process: Condensation)

WSC (8.9 g, 46.3 mmol), dimethylaminopyridine (1.08 g, 0.4 mmol), and 2-butyloctane-1-ol (16.4 g, 88.2 mmol) were added to a solution obtained by dissolving the seventh process product (20.0 g, 44.1 mmol) in methylene chloride (220.0 mL). After the solution was stirred at room temperature until the next day, water was added thereto, and the organic layer was subjected to liquid separation. The organic layer was washed with water five times and dried over anhydrous magnesium sulfate. A drying agent was removed by filtration, and the filtrate was concentrated under reduced pressure. The resultant was purified by silica gel column chromatography, thereby obtaining YS-120 (22.0 g, 35.4 mmol) represented by Formula (6).

Example 17

Synthesis of 1-((2Z,5Z)-deca-2,5-diene-1-yloxy)-1-oxoicosane-10-yl-1-methylpiperidine-4-carboxylate (hereinafter, also referred to as "YS-121")

YS-121 represented by the following Formula (24) was synthesized in the same manner as in Example 16 except that (2Z,5Z)-deca-2,5-diene-1-ol was reacted in place of 2-butyloctane-1-ol in the eighth process.

(24)

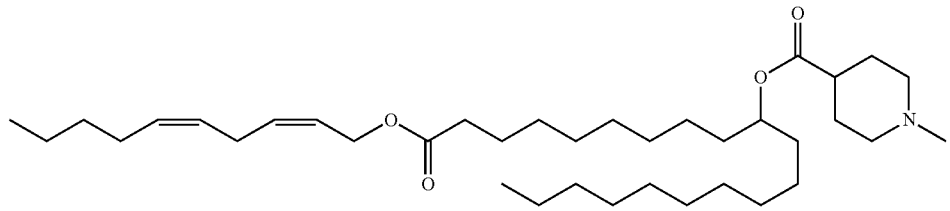

ESI-MS (M+H) cacld 589.5, found 590.7, $^1$H NMR (400 MHz, CDCl$_3$) δ5.60 (1H, m), 5.36 (1H, m), 4.87 (1H, tt), 4.64 (1H, d), 2.86 (2H, m), 2.36 (3H, s) 2.32 (2H, t), 2.22 (1H, m), 2.02 (2H, m), 1.97 (2H, m), 1.61 (2H, m), 1.50 (3H, m), 1.27 (40H, m), 0.88 (6H, m)

Example 18

Synthesis of (Z)-1-((2-butylnon-3-en-1-yl)oxy)-1-oxoicosane-10-yl-1-methylpiperidine-4-carboxylate (hereinafter, also referred to as "YS-122")

YS-122 represented by the following Formula (25) was synthesized in the same manner as in Example 16 except that (Z)-2-butylnon-3-en-1-ol was reacted in place of 2-butyloctane-1-ol in the eighth process.

(25)

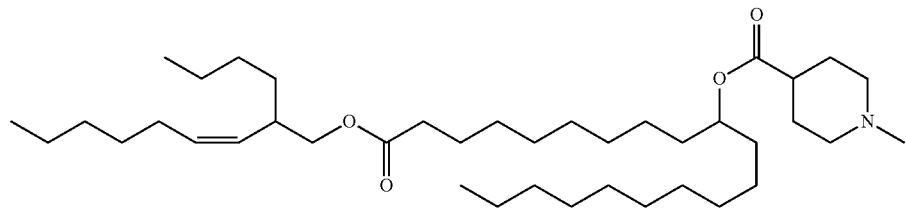

ESI-MS (M+H) cacld 633.6, found 634.7, $^1$H NMR (400 MHz, CDCl$_3$) δ5.60 (1H, m), 5.36 (1H, m), 4.87 (1H, tt), 4.64 (1H, d), 2.86 (2H, m), 2.36 (3H, s), 2.32 (2H, t), 2.22 (1H, m), 2.02 (2H, m), 1.97 (2H, m), 1.61 (2H, m), 1.50 (3H, m), 1.27 (48H, m), 0.88 (6H, m)

As described below, when a lipid complex is formed by the compound represented by Formula (25), an increase in particle diameter of the lipid complex in a case of being stored for a certain period is suppressed so that the stability is high.

Example 19

Synthesis of (Z)-1-oxo-1-((5-propylnon-2-en-1-yl)oxy)icosane-10-yl-1-methylpiperidine-4-carboxylate (hereinafter, also referred to as "YS-123")

YS-123 represented by the following Formula (26) was synthesized in the same manner as in Example 16 except that (Z)-5-propylnon-2-en-1-ol was reacted in place of 2-butyloctane-1-ol in the eighth process.

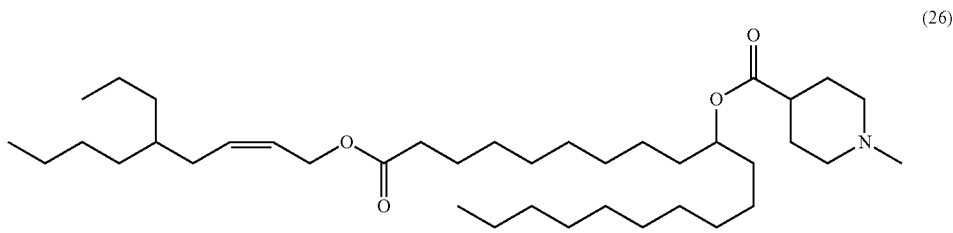 [SMILES: CCCCCCCCCCC(CCCCCCCCC(=O)OC/C=C\CC(CCC)CCCC)OC(=O)C1CCN(C)CC1]

(26)

ESI-MS (M+H) cacld 619.6, found 620.7, $^1$H NMR (400 MHz, CDCl$_3$) δ5.60 (2H, m), 4.87 (1H, tt), 4.61 (2H, d), 2.93 (2H, d), 2.42 (3H, s), 2.31 (2H, t), 2.29 (2H, t), 2.05 (4H, t), 1.93 (2H, m), 1.61 (2H, m), 1.50 (4H, m), 1.27 (43H, m), 0.88 (6H, m)

As described below, when a lipid complex is formed by the compound represented by Formula (26), an increase in particle diameter of the lipid complex in a case of being stored for a certain period is suppressed so that the stability is high.

Example 20

Synthesis of 1-oxo-1-((3-pentyloctyl)oxy)icosane-10-yl-1-methylpiperidine-4-carboxylate (hereinafter, also referred to as "YS-124")

YS-124 represented by the following Formula (27) was synthesized in the same manner as in Example 16 except that 3-pentyloctane-1-ol was reacted in place of 2-butyloctane-1-ol in the eighth process.

ESI-MS (M+H) cacld 635.6, found 636.7, $^1$H NMR (400 MHz, CDCl$_3$) δ4.87 (1H, tt), 4.06 (2H, m), 2.81 (2H, d), 2.27 (6H, m), 2.02 (2H, m), 1.97 (2H, m), 1.77 (4H, m), 1.61 (2H, m), 1.50 (3H, m), 1.43 (1H, m), 1.27 (43H, m), 0.88 (9H, m)

As described below, when a lipid complex is formed by the compound represented by Formula (27), an increase in particle diameter of the lipid complex in a case of being stored for a certain period is suppressed so that the stability is high.

Example 21

Synthesis of 1-((2,4-dipropylheptyl)oxy)-1-oxoicosane-10-yl-1-methylpiperidine-4-carboxylate (hereinafter, also referred to as "YS-125")

YS-125 represented by the following Formula (28) was synthesized in the same manner as in Example 16 except that 2,4-dipropylheptane-1-ol was reacted in place of 2-butyloctane-1-ol in the eighth process.

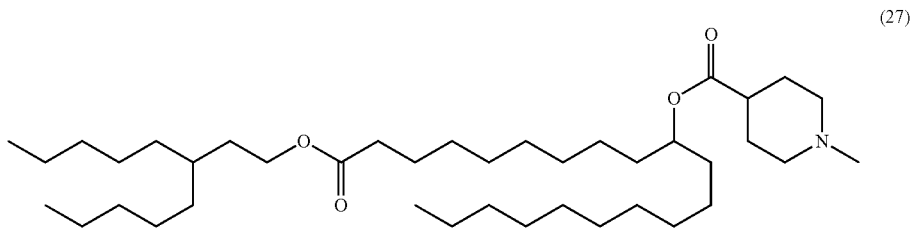 [SMILES: CCCCCCCCCCC(CCCCCCCCC(=O)OCCC(CCCCC)CCCCC)OC(=O)C1CCN(C)CC1]

(27)

(28)

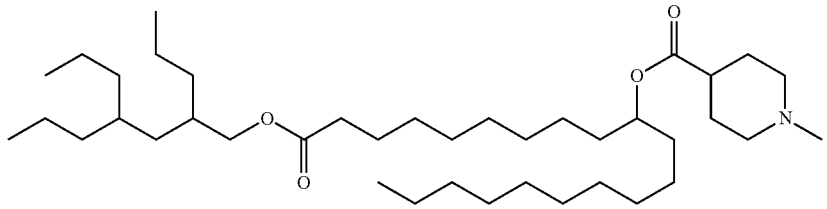

ESI-MS (M+H) cacld 635.6, found 636.7, $^1$H NMR (400 MHz, CDCl$_3$) δ4.87 (1H, tt), 3.95 (1H, d), 3.55 (2H, t), 2.96 (2H, m), 2.45 (3H, s), 2.32 (2H, t), 2.22 (1H, m), 2.02 (2H, m), 1.97 (2H, m), 1.61 (2H, m), 1.50 (3H, m), 1.27 (49H, m), 0.88 (12H, m)

As described below, when a lipid complex is formed by the compound represented by Formula (28), an increase in particle diameter of the lipid complex in a case of being stored for a certain period is suppressed so that the stability is high.

Example 22

Synthesis of 1-((3,4-dipropylheptyl)oxy)-1-oxoicosane-10-yl-1-methylpiperidine-4-carboxylate (hereinafter, also referred to as "YS-126")

YS-126 represented by the following Formula (29) was synthesized in the same manner as in Example 16 except that 3,4-dipropylheptane-1-ol was reacted in place of 2-butyloctane-1-ol in the eighth process.

(29)

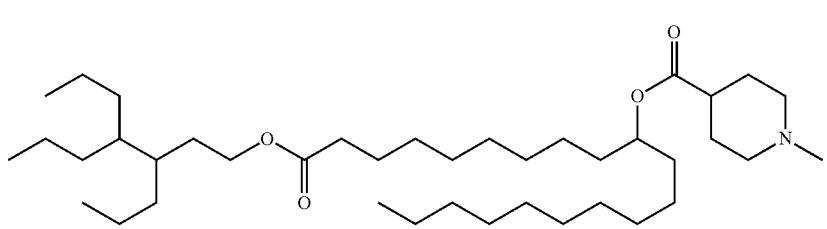

ESI-MS (M+H) cacld 635.6, found 636.7, $^1$H NMR (400 MHz, CDCl$_3$) δ4.87 (1H, tt), 4.06 (2H, m), 3.00 (2H, m), 2.45 (5H, m), 2.27 (2H, t), 2.02 (2H, m), 1.97 (2H, m), 1.61 (2H, m), 1.50 (3H, m), 1.43 (2H, m), 1.27 (42H, m), 0.88 (12H, m)

As described below, when a lipid complex is formed by the compound represented by Formula (29), an increase in particle diameter of the lipid complex in a case of being stored for a certain period is suppressed so that the stability is high.

Example 23

Synthesis of 1-(4-(hexyldisulfanyl)-3-((hexyldisulfanyl)methyl)butoxy)-1-oxoicosane-10-yl-1-methyl piperidine-4-carboxylate (hereinafter, also referred to as "YS-127")

YS-127 represented by the following Formula (30) was synthesized in the same manner as in Example 16 except that 4-(hexyldisulfanyl)-3-((hexyldisulfanyl)methyl)butane-1-ol was reacted in place of 2-butyloctane-1-ol in the eighth process.

(30)

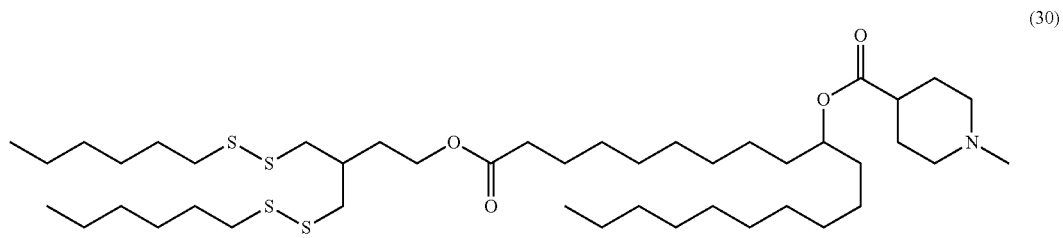 [SMILES: CCCCCCCCCCC(CCCCCCCCC(=O)OCCC(CSSCCCCCC)CSSCCCCCC)OC(=O)C1CCN(C)CC1]

ESI-MS (M+H) cacld 819.5, found 820.6, $^1$H NMR (400 MHz, CDCl$_3$) δ4.86 (1H, tt), 4.13 (2H, t), 2.81 (6H, d), 2.67 (2H, t), 2.29 (3H, t), 2.27 (3H, s), 1.99 (2H, m), 1.90 (2H, dd), 1.79 (2H, dt), 1.68 (12H, m), 1.50 (6H, m), 1.42 (6H, m), 1.24 (29H, m), 0.88 (9H, m)

Example 24

Synthesis of 1-((6-(butyldisulfanyl)-3-(3-(butyldisulfanyl)propyl)hexyl)oxy)-1-oxoicosane-10-yl-1-methylpiperidine-4-carboxylate (hereinafter, also referred to as "YS-128")

YS-128 represented by the following Formula (31) was synthesized in the same manner as in Example 16 except that 6-(butyldisulfanyl)-3-(3-(butyldisulfanyl)propyl)hexane-1-ol was reacted in place of 2-butyloctane-1-ol in the eighth process.

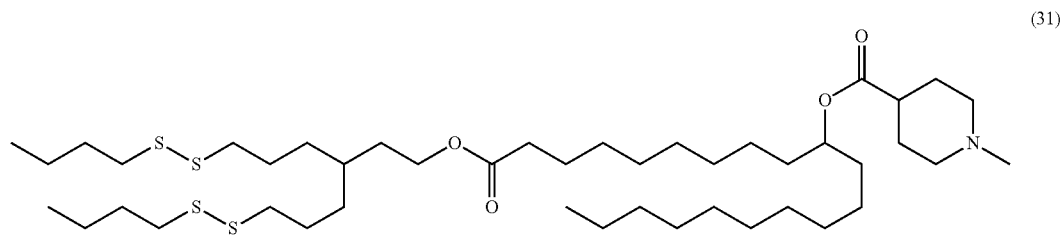 [SMILES: CCCCCCCCCCC(CCCCCCCCC(=O)OCCC(CCCSSCCCC)CCCSSCCCC)OC(=O)C1CCN(C)CC1]

(31)

ESI-MS (M+H) cacld 819.5, found 821.0, 1H NMR (400 MHz, CDCl$_3$) δ4.86 (1H, tt), 4.08 (2H, t), 2.81 (2H, d), 2.67 (8H, dd), 2.29 (3H, t), 2.27 (3H, s), 1.99 (2H, m), 1.90 (2H, dd), 1.79 (2H, dt), 1.68 (12H, m), 1.50 (6H, m), 1.42 (6H, m), 1.24 (37H, m), 0.92-0.88 (9H, m)

Example 25

Synthesis of 1-((2-butyloctyl)oxy)-1-oxoicosane-10-yl-1-methylpiperidine-3-carboxylate (hereinafter, also referred to as "YS-129")

YS-129 represented by the following Formula (32) was synthesized in the same manner as in Example 16 except that 1-methylpyrrolidine-3-carboxylic acid was reacted in place of 1-methylpiperidine-4-carboxylic acid in the sixth process.

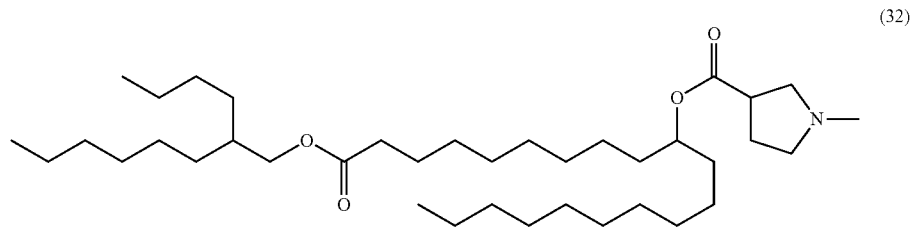 [SMILES: CCCCCCCCCCC(CCCCCCCCC(=O)OCC(CCCC)CCCCCC)OC(=O)C1CCN(C)C1]

(32)

ESI-MS (M+H) cacld 607.6, found 608.8, $^1$H NMR (400 MHz, CDCl$_3$) 54.86 (1H, tt), 3.98 (2H, d), 3.05 (1H, tt), 2.86 (1H, tt), 2.67 (2H, m), 2.49 (1H, tt), 2.35 (3H, s) 2.29 (2H, t), 2.17 (2H, m), 1.72 (2H, s), 1.60 (3H, m), 1.50 (4H, m), 1.24 (44H, m), 0.92-0.88 (9H, m)

Example 26

Synthesis of 1-((2-butyloctyl)oxy)-1-oxoicosane-10-yl-1-methylazetidine-3-carboxylate (hereinafter, also referred to as "YS-131")

YS-131 represented by the following Formula (33) was synthesized in the same manner as in Example 16 except that 1-methylazetidine-3-carboxylic acid was reacted in place of 1-methylpiperidine-4-carboxylic acid in the sixth process.

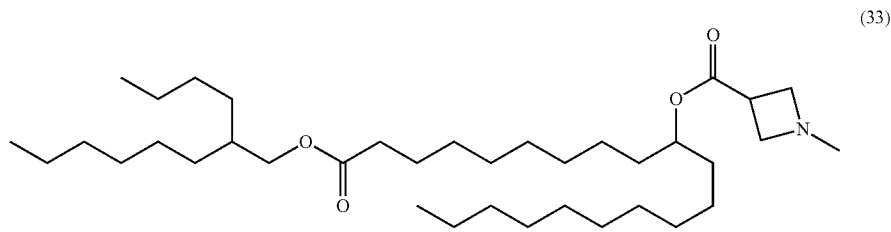 [SMILES: CCCCCCCCCCC(CCCCCCCCC(=O)OCC(CCCC)CCCCCC)OC(=O)C1CN(C)C1]

(33)

ESI-MS (M+H) cacld 593.4, found 594.7, $^1$H NMR (400 MHz, CDCl$_3$) δ4.87 (1H, tt), 3.96 (2H, d), 3.57 (2H, d), 3.25 (2H, d), 3.23 (1H, tt), 2.32 (3H, s), 2.29 (2H, t), 2.03 (2H, m), 1.61 (4H, m), 1.49 (4H, m), 1.27-1.21 (41H, m), 0.87 (9H, m)

Example 27

Synthesis of 1-((2-butyloctyl)oxy)-1-oxoicosane-10-yl-1-ethylpiperidine-4-carboxylate (hereinafter, also referred to as "YS-132")

YS-132 represented by the following Formula (34) was synthesized in the same manner as in Example 16 except that 1-ethylpiperidine-4-carboxylic acid was reacted in place of 1-methylpiperidine-4-carboxylate in the sixth process.

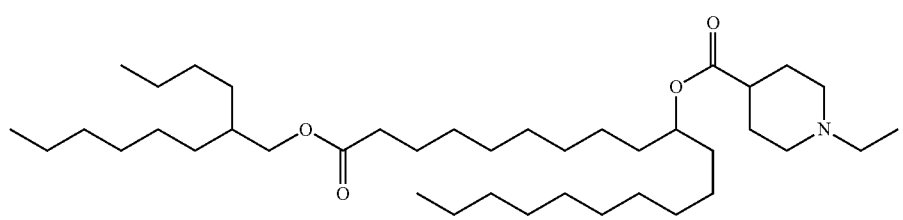

(34)

ESI-MS(M+H) cacld 636.0, found 636.7, $^1$H NMR (400 MHz, CDCl$_3$) δ4.87 (1H, ddd), 3.96 (2H, d), 2.91 (2H, d), 2.40 (2H, dd), 2.29 (4H, m), 2.03-1.93 (4H, m), 1.80 (2H, m), 1.61 (4H, m), 1.49 (4H, m), 1.27-1.21 (41H, m), 1.08 (4H, t), 0.87 (9H, m)

Example 28

Synthesis of 2-butyloctyl-10-((4-(dimethylamino)butanoyl)oxy)icosanoate (hereinafter, also referred to as "YS-133")

YS-133 represented by the following Formula (35) was synthesized in the same manner as in Example 16 except that 4-(dimethylamino)butanoic acid was reacted in place of 1-methylpiperidine-4-carboxylic acid in the sixth process.

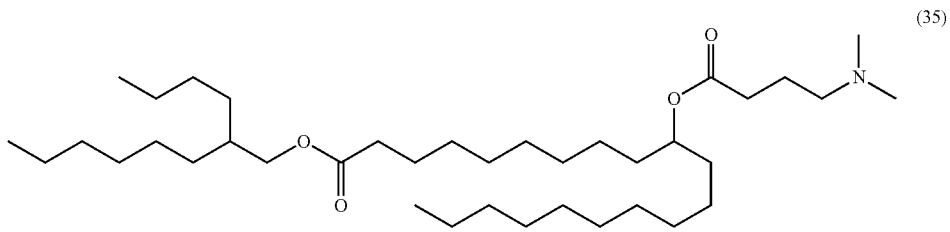 [SMILES: CCCCCCCCCCC(CCCCCCCCC(=O)OCC(CCCC)CCCCCC)OC(=O)CCCN(C)C]

ESI-MS (M+H) cacld 609.6, found 610.7, $^1$H NMR (400 MHz, CDCl$_3$) δ4.86 (1H, tt), 3.96 (2H, d), 2.33-2.26 (6H, m), 2.21 (6H, s), 2.03 (2H, m), 1.80 (2H, m), 1.61 (4H, m), 1.49 (4H, m), 1.27-1.21 (41H, m), 0.87 (9H, m)

<Preparation (1) of Composition>

Example 29

(YS-102)

A composition was prepared using the cationic lipid (YS-102) of Example 1. An annealed nucleic acid (GeneDesign, Inc., hereinafter, also referred to as "Factor VII siRNA") serving as siRNA formed of a base sequence of the sense strand 5'-GGAfUfCAfUfCfUfCAAGfUfCfUfUAfCT*T-3' (SEQ ID NO: 1, T: DNA, fU, fC=2'-Fluoro RNA, *=Phosphorothioate linkage) and the antisense strand 5'-GfUAAGAfCfUfUGAGAfUGAfUfCfCT*T-3' (SEQ ID NO: 2, T: DNA, fU, fC=2'-Fluoro RNA, *=Phosphorothioate linkage) and which suppresses the expression of Factor VII (blood coagulation factor VII) genes was used as the nucleic acid.

Factor VII siRNA was dissolved in 25 mM sodium acetate (pH of 4.0) to have an amount of 216 μg/mL, and then an siRNA diluent was obtained. Further, the cationic lipid (YS-102), DSPC (Nippon Fine Chemical Co., Ltd.), cholesterol (Nippon Fine Chemical Co., Ltd.), and MPEG2000-DMG (NOF CORPORATION) were dissolved in ethanol at a ratio of 60/8.5/30/1.5 (molar ratio) so that the total lipid concentration was set to 15 mM, and then a lipid solution was obtained. The siRNA diluent and the lipid solution were mixed with each other respectively at a flow rate of 2.4 mL/min and at a flow rate of 1.29 mL/min, and then 25 mM sodium acetate (pH of 4.0) was further mixed with the solution at a flow rate of 9.25 mL/min, thereby obtaining a lipid complex aqueous solution. The obtained lipid complex aqueous solution was subjected to dialysis using a dialysis membrane (trade name "Float-A-Lyzer G2", SPECTRUM, Inc., 50K MWCO), and the external liquid was replaced by a phosphate buffer (PBS, pH of 7.5). After the dialysis, concentration and filter sterilization were performed, thereby obtaining a composition of Example 29.

Example 30

(YS-101)

A composition of Example 30 was obtained in the same manner as in Example 29 except that the cationic lipid (YS-101) of Example 2 was used as the cationic lipid in place of YS-102.

Example 31

(YS-103)

A composition of Example 31 was obtained in the same manner as in Example 29 except that the cationic lipid (YS-103) of Example 3 was used as the cationic lipid in place of YS-102.

Reference Example 1

(YS-021)

A composition of Reference Example 1 was obtained in the same manner as in Example 29 except that 1-(2-octylcyclopropyl)heptadecane-8-yl-1-methylpiperidine-4-carboxylate (hereinafter, also referred to as "YS-021") represented by the following Formula (36) was used as the cationic lipid in place of YS-102.

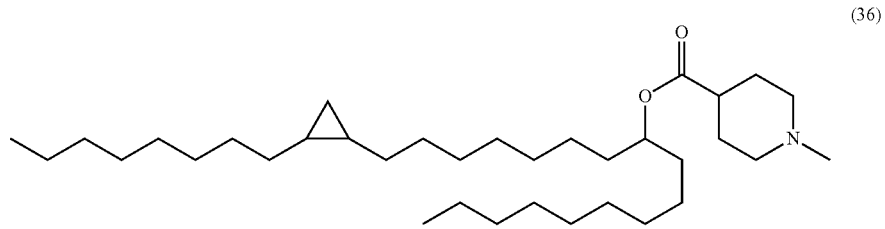 [SMILES: CCCCCCCCCC(CCCCCCCC1CC1CCCCCCCC)OC(=O)C1CCN(C)CC1]

<Analysis (1) of Composition>

In the compositions of Examples 29 to 31 and Reference Example 1, the encapsulation rate of siRNA into the lipid complex was measured.

Specifically, the composition was diluted with RNase Free Water, an siRNA concentration (A) measured using Quant-iT RiboGreen RNA Reagent (Invitrogen Corporation) was set as the concentration of siRNA present in the external liquid of the lipid complex. Further, an siRNA concentration (B) measured by diluting the composition with 1% Triton X-100 was set as the total siRNA concentration in the composition. Next, the encapsulation rate of the nucleic acid was calculated according to the following Equation (F1).

Encapsulation rate (%)=100−(A/B)×100(F1)

Further, the average particle diameter of the lipid complex was measured using a particle diameter-measuring device (trade name "Zetasizer Nano ZS", manufactured by Malvern Instruments Ltd.).

The encapsulation rate of siRNA and the average particle diameter (Z-average) of the lipid complex are listed in Table 1.

TABLE 1

| Composition | Cationic lipid | Encapsulation rate (%) | Average particle diameter (nm) |
|---|---|---|---|
| Example 29 | YS-102 | 98 | 74 |
| Example 30 | YS-101 | >99 | 79 |
| Example 31 | YS-103 | 98 | 68 |
| Reference Example 1 | YS-021 | >99 | 65 |

<Preparation (2) of Composition>

Example 32

(YS-111)

A composition was prepared using the cationic lipid (YS-111) of Example 5. Factor VII siRNA, which was the same as the nucleic acid used for the composition of Example 29, was used as the nucleic acid.

Factor VII siRNA was dissolved in 25 mM sodium acetate (pH of 4.0) to have an amount of 181 μg/mL, and then an siRNA diluent was obtained. Further, the cationic lipid (YS-111), DSPC (Nippon Fine Chemical Co., Ltd.), cholesterol (Nippon Fine Chemical Co., Ltd.), and MPEG2000-DMG (NOF CORPORATION) were dissolved in ethanol at a ratio of 60/8.5/30/1.5 (molar ratio) so that the total lipid concentration was set to 10 mM, and then a lipid solution was obtained. The siRNA diluent and the lipid solution were mixed with each other respectively at a flow rate of 2.4 mL/min and at a flow rate of 1.29 mL/min, and then 25 mM sodium acetate (pH of 4.0) was further mixed with the solution at a flow rate of 5.0 mL/min, thereby obtaining a lipid complex aqueous solution. The obtained lipid complex aqueous solution was subjected to dialysis using a dialysis membrane (trade name "Float-A-Lyzer G2", SPECTRUM, Inc., 50K MWCO), and the external liquid was replaced by a phosphate buffer (PBS, pH of 7.5). After the dialysis, concentration and filter sterilization were performed, thereby obtaining a composition of Example 32.

Example 33

(YS-112)

A composition of Example 33 was obtained in the same manner as in Example 32 except that the cationic lipid (YS-112) of Example 6 was used as the cationic lipid in place of YS-111.

Example 34

(YS-113)

A composition of Example 34 was obtained in the same manner as in Example 32 except that the cationic lipid (YS-113) of Example 7 was used as the cationic lipid in place of YS-111.

Example 35

(YS-114)

A composition of Example 35 was obtained in the same manner as in Example 32 except that the cationic lipid (YS-114) of Example 8 was used as the cationic lipid in place of YS-111.

Example 36

(YS-115)

A composition of Example 36 was obtained in the same manner as in Example 32 except that the cationic lipid (YS-115) of Example 9 was used as the cationic lipid in place of YS-111.

Example 37

(YS-116)

A composition of Example 36 was obtained in the same manner as in Example 32 except that the cationic lipid (YS-116) of Example 10 was used as the cationic lipid in place of YS-111.

Comparative Example 1

(ALN-319)

A composition of Comparative Example 1 was obtained in the same manner as in Example 32 except that di((Z)-non-2-en-1-yl) 9-((4-(dimethylamino)butanoyl)oxy)heptadecanedioate (hereinafter, also referred to as "ALN-319") represented by the following Formula (32), which is described in PTL 1, was synthesized according to the method described in PTL 1 and then used as the cationic lipid in place of YS-111.

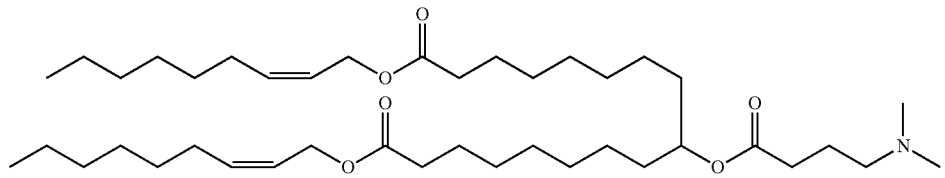

(32)

<Analysis (2) of Composition>

In the compositions of Examples 32 to 37 and Comparative Example 1, the encapsulation rate of siRNA into the lipid complex and the average particle diameter of the lipid complex were measured in the same manner as those for the composition of Example 29. The encapsulation rate of siRNA and the average particle diameter (Z-average) of the lipid complex are listed in Table 2.

TABLE 2

| Composition | Cationic lipid | Encapsulation rate (%) | Average particle diameter (nm) |
|---|---|---|---|
| Example 32 | YS-111 | 95 | 78 |
| Example 33 | YS-112 | 94 | 71 |
| Example 34 | YS-113 | 88 | 70 |
| Example 35 | YS-114 | 86 | 73 |
| Example 36 | YS-115 | 95 | 68 |
| Example 37 | YS-116 | 91 | 72 |
| Comparative Example 1 | ALN-319 | 96 | 77 |

Preparation (3) of Composition

Example 38

(YS-117)

A composition was prepared using the cationic lipid (YS-117) of Example 11. Factor VII siRNA, which was the same as the nucleic acid used for the composition of Example 29, was used as the nucleic acid.

Factor VII siRNA was dissolved in 25 mM sodium acetate (pH of 4.0) to have an amount of 108 µg/mL, and then an siRNA diluent was obtained. Further, the cationic lipid (YS-111), DSPC (Nippon Fine Chemical Co., Ltd.), cholesterol (Nippon Fine Chemical Co., Ltd.), and MPEG2000-DMG (NOF CORPORATION) were dissolved in ethanol at a ratio of 60/8.5/30/1.5 (molar ratio) so that the total lipid concentration was set to 6 mM, and then a lipid solution was obtained. The siRNA diluent and the lipid solution were mixed with each other respectively at a flow rate of 2.4 mL/min and at a flow rate of 1.29 mL/min, and then 25 mM sodium acetate (pH of 4.0) was further mixed with the solution at a flow rate of 9.25 mL/min, thereby obtaining a lipid complex aqueous solution. The obtained lipid complex aqueous solution was subjected to dialysis using a dialysis membrane (trade name "Float-A-Lyzer G2", SPECTRUM, Inc., 50K MWCO), and the external liquid was replaced by a phosphate buffer (PBS, pH of 7.5). After the dialysis, concentration and filter sterilization were performed, thereby obtaining a composition of Example 38.

Example 39

(YS-117S)

A composition of Example 39 was obtained in the same manner as in Example 38 except that the cationic lipid (YS-117S) of Example 12 was used as the cationic lipid in place of YS-117.

Example 40

(YS-118)

A composition of Example 40 was obtained in the same manner as in Example 38 except that the cationic lipid (YS-118) of Example 13 was used as the cationic lipid in place of YS-117.

Example 41

(YS-118S)

A composition of Example 41 was obtained in the same manner as in Example 38 except that the cationic lipid (YS-118S) of Example 14 was used as the cationic lipid in place of YS-117.

Example 42

(YS-119)

A composition of Example 42 was obtained in the same manner as in Example 38 except that the cationic lipid (YS-119) of Example 4 was used as the cationic lipid in place of YS-117.

<Analysis (3) of Composition>

In the compositions of Examples 38 to 42, the encapsulation rate of siRNA into the lipid complex and the average particle diameter of the lipid complex were measured in the same manner as those for the composition of Example 29. The encapsulation rate of siRNA and the average particle diameter (Z-average) of the lipid complex are listed in Table 3.

TABLE 3

| Composition | Cationic lipid | Encapsulation rate (%) | Average particle diameter (nm) |
|---|---|---|---|
| Example 38 | YS-117 | 58 | 110 |
| Example 39 | YS-117S | 65 | 126 |
| Example 40 | YS-118 | 74 | 74 |
| Example 41 | YS-118S | 73 | 71 |
| Example 42 | YS-119 | 77 | 72 |

Preparation (4) of Composition

Example 43

(YS-119)

A composition was prepared using the cationic lipid (YS-119) of Example 4. Factor VII siRNA, which was the same as the nucleic acid used for the composition of Example 29, was used as the nucleic acid.

Factor VII siRNA was dissolved in 25 mM sodium acetate (pH of 4.0) to have an amount of 108 µg/mL, and then an siRNA diluent was obtained. Further, the cationic lipid (YS-119), DSPC (Nippon Fine Chemical Co., Ltd.), cholesterol (Nippon Fine Chemical Co., Ltd.), and MPEG2000-DMG (NOF CORPORATION) were dissolved in ethanol at a ratio of 60/8.5/30/1.5 (molar ratio) so that the total lipid concentration was set to 6 mM, and then a lipid solution was obtained. The siRNA diluent and the lipid solution were mixed with each other respectively at a flow rate of 1.80 mL/min and at a flow rate of 0.97 mL/min, and then 25 mM sodium acetate (pH of 4.0) was further mixed with the solution at a flow rate of 6.94 mL/min, thereby obtaining a lipid complex aqueous solution. The obtained lipid complex aqueous solution was subjected to dialysis using a dialysis membrane (trade name "Float-A-Lyzer G2", SPECTRUM, Inc., 50K MWCO), and the external liquid was replaced by a phosphate buffer (PBS, pH of 7.5). After the dialysis, concentration and filter sterilization were performed, thereby obtaining a composition of Example 43.

Comparative Example 2

(ALN-319)

A composition of Comparative Example 2 was obtained in the same manner as in Example 43 except that ALN-319 described above was used as the cationic lipid in place of YS-119.

<Analysis (4) of Composition>

In the compositions of Example 43 and Comparative Example 2, the encapsulation rate of siRNA into the lipid complex and the average particle diameter (Z-average) of the lipid complex were measured in the same manner as those for the composition of Example 29. The encapsulation rate of siRNA and the average particle diameter of the lipid complex are listed in Table 4.

TABLE 4

| Composition | Cationic lipid | Encapsulation rate (%) | Average particle diameter (nm) |
|---|---|---|---|
| Example 43 | YS-119 | 88 | 94 |
| Comparative Example 2 | ALN-319 | 75 | 95 |

Preparation (5) of Composition

Example 44

(YS-119)

A composition was prepared using the cationic lipid (YS-119) of Example 4. Factor VII siRNA, which was the same as the nucleic acid used for the composition of Example 29, was used as the nucleic acid.

Factor VII siRNA was dissolved in 25 mM sodium acetate (pH of 4.0) to have an amount of 216 µg/mL, and then an siRNA diluent was obtained. Further, the cationic lipid (YS-119), cholesterol (Nippon Fine Chemical Co., Ltd.), and MPEG2000-DPG (NOF CORPORATION) were dissolved in ethanol at a ratio of 60/38.5/1.5 (molar ratio) so that the total lipid concentration was set to 6 mM, and then a lipid solution was obtained. The siRNA diluent and the lipid solution were mixed with each other respectively at a flow rate of 3.36 mL/min and at a flow rate of 1.81 mL/min, and then 25 mM sodium acetate (pH of 4.0) was further mixed with the solution at a flow rate of 12.95 mL/min, thereby obtaining a lipid complex aqueous solution. The obtained lipid complex aqueous solution was subjected to dialysis using a dialysis membrane (trade name "Float-A-Lyzer G2", SPECTRUM, Inc., 50K MWCO), and the external liquid was replaced by a phosphate buffer (PBS, pH of 7.5). After the dialysis, concentration and filter sterilization were performed, thereby obtaining a composition of Example 44.

Example 45

(YS-120)

A composition of Example 45 was obtained in the same manner as in Example 44 except that the cationic lipid (YS-120) of Example 15 was used as the cationic lipid in place of YS-119.

<Analysis (5) of Composition>

In the compositions of Examples 44 and 45, the encapsulation rate of siRNA into the lipid complex and the average particle diameter (Z-average) of the lipid complex were measured in the same manner as those for the composition of Example 29. The encapsulation rate of siRNA and the average particle diameter of the lipid complex are listed in Table 5.

TABLE 5

| Composition | Cationic lipid | Encapsulation rate (%) | Average particle diameter (nm) |
|---|---|---|---|
| Example 44 | YS-119 | 96 | 80 |
| Example 45 | YS-120 | 94 | 79 |

Preparation (6) of Composition

Example 46

(YS-120)

A composition was prepared using the cationic lipid (YS-120) of Example 16. Factor VII siRNA, which was the same as the nucleic acid used for the composition of Example 29, was used as the nucleic acid.

Factor VII siRNA was dissolved in 25 mM sodium acetate (pH of 4.0) to have an amount of 450 µg/mL, and then an siRNA diluent was obtained. Further, the cationic lipid (YS-120), DSPC (Nippon Fine Chemical Co., Ltd.), cholesterol (Nippon Fine Chemical Co., Ltd.), and MPEG2000-DMG (NOF CORPORATION) were dissolved in ethanol at a ratio of 60/8.5/30/1.5 (molar ratio) so that the total lipid concentration was set to 40 mM, and then a lipid solution was obtained. The mass ratio of the lipids to siRNA was set to 0.06, and the siRNA diluent and the lipid solution were mixed with each other respectively at a flow rate of 4.0 mL/min and at a flow rate of 1.3 mL/min, thereby obtaining a lipid complex aqueous solution. The obtained lipid complex aqueous solution was subjected to dialysis using a dialysis membrane (trade name "Float-A-Lyzer G2", SPECTRUM, Inc., 50K MWCO), and the external liquid was replaced by a phosphate buffer (PBS, pH of 7.4). After the dialysis, concentration and filter sterilization were performed, thereby obtaining a composition of Example 46.

Example 47

(YS-121)

A composition of Example 47 was obtained in the same manner as in Example 46 except that the cationic lipid (YS-121) of Example 17 was used as the cationic lipid in place of YS-120.

Example 48

(YS-122)

A composition of Example 48 was obtained in the same manner as in Example 46 except that the cationic lipid (YS-122) of Example 18 was used as the cationic lipid in place of YS-120.

Example 49

(YS-123)

A composition of Example 49 was obtained in the same manner as in Example 46 except that the cationic lipid (YS-123) of Example 19 was used as the cationic lipid in place of YS-120.

Example 50

(YS-124)

A composition of Example 50 was obtained in the same manner as in Example 46 except that the cationic lipid (YS-124) of Example 20 was used as the cationic lipid in place of YS-120.

Example 51

(YS-125)

A composition of Example 51 was obtained in the same manner as in Example 46 except that the cationic lipid (YS-125) of Example 21 was used as the cationic lipid in place of YS-120.

Example 52

(YS-126)

A composition of Example 52 was obtained in the same manner as in Example 46 except that the cationic lipid (YS-126) of Example 22 was used as the cationic lipid in place of YS-120.

<Analysis (6) of Composition>

In the compositions of Examples 46 to 52, the encapsulation rate of siRNA into the lipid complex and the average particle diameter (Z-average) of the lipid complex were measured in the same manner as those for the composition of Example 29. The encapsulation rate of siRNA and the average particle diameter of the lipid complex are listed in Table 6.

TABLE 6

| Composition | Cationic lipid | Encapsulation rate (%) | Average particle diameter (nm) |
|---|---|---|---|
| Example 46 | YS-120 | 99 | 64 |
| Example 47 | YS-121 | 84 | 74 |
| Example 48 | YS-122 | 98 | 66 |
| Example 49 | YS-123 | 99 | 61 |
| Example 50 | YS-124 | 99 | 64 |
| Example 51 | YS-125 | 96 | 63 |
| Example 52 | YS-126 | 99 | 63 |

<Analysis (7) of Composition>

In the compositions of Examples 46 to 52, each composition was stored in a sealed vial at 4° C. and the particle diameter (Z-average and polydispersity index) before the strorage, after 3 months from the storage and after 6 months from the storage was measured in the same manner as that for the composition of Example 29.

Table 7 shows a change in average particle diameter of the compositions of Examples 46 to 52 with time and a change (d) in particle diameter thereof after 6 months from the storage and before the storage. In a case of the compositions containing cationic lipids other than YS-121, it was shown that an increase in particle diameter of the lipid complex was suppressed during the storage period.

Example 54

(YS-124)

A composition of Example 54 was obtained in the same manner as in Example 53 except that the cationic lipid (YS-127) of Example 23 was used as the cationic lipid in place of YS-120.

Comparative Example 3

(ALN-319)

A composition of Comparative Example 3 was obtained in the same manner as in Example 53 except that ALN-319 described above was used as the cationic lipid in place of YS-120.

<Analysis (8) of Composition>

In the compositions of Examples 53 and 54 and Comparative Example 3, the encapsulation rate of siRNA into the lipid complex and the average particle diameter (Z-average) of the lipid complex were measured in the same manner as those for the composition of Example 29. The encapsulation rate of siRNA and the average particle diameter of the lipid complex are listed in Table 8.

TABLE 8

| Composition | Cationic lipid | Encapsulation rate (%) | Average particle diameter (nm) |
|---|---|---|---|
| Example 53 | YS-120 | 97 | 66 |
| Example 54 | YS-124 | 96 | 67 |
| Comparative Example 3 | ALN-319 | 98 | 95 |

<Analysis (9) of Composition>

In the compositions of Examples 53 and 54 and Comparative Example 3, the particle diameter (Z-average and polydispersity index) was measured immediately after the lipid complex was generated by mixing the siRNA diluent and the lipid solution in the preparation of each composition, after the lipid complex was dialyzed into PBS, and after storage in the sealed vial at 4° C. for 2 months and 6 months, using a particle diameter-measuring device (trade name

TABLE 7

| | | Before storage | | After 3 months | | After 6 months | | |
|---|---|---|---|---|---|---|---|---|
| Composition | Cationic lipid | Average particle diameter (nm) | Polydispersity index | Average particle diameter (nm) | Polydispersity index | Average particle diameter (nm) | Polydispersity index | d(nm) |
| Example 46 | YS-120 | 64.4 | 0.04 | 64.7 | 0.05 | 66.7 | 0.05 | 2.3 |
| Example 47 | YS-121 | 74.2 | 0.03 | 86.5 | 0.06 | 98.0 | 0.07 | 23.8 |
| Example 48 | YS-122 | 65.5 | 0.06 | 65.4 | 0.08 | 64.6 | 0.05 | −0.9 |
| Example 49 | YS-123 | 60.9 | 0.03 | 63.5 | 0.06 | 65.3 | 0.07 | 4.4 |
| Example 50 | YS-124 | 64.4 | 0.04 | 63.6 | 0.04 | 62.5 | 0.07 | −1.9 |
| Example 51 | YS-125 | 63.3 | 0.01 | 62.3 | 0.12 | 62.4 | 0.06 | −0.9 |
| Example 52 | YS-126 | 62.9 | 0.05 | 65.8 | 0.08 | 64.0 | 0.04 | 1.1 |

Preparation (7) of Composition

Example 53

(YS-120)

A composition was prepared using the cationic lipid (YS-120) of Example 16 in the same manner as in the "preparation (6) of composition".

"Zetasizer Nano ZS", manufactured by Malvern Instruments Ltd.).

Table 9 shows a change in average particle diameter of the compositions of Examples 53 and 54 and Comparative Example 3 with time and a change (d) in particle diameter thereof after 6 months from the storage and immediately after the mixture. In a case of the compositions containing the cationic lipid YS-120 or YS-124, it was shown that an increase in particle diameter of the lipid complex was suppressed during the storage period compared to the composition of Comparative Example 3.

TABLE 9

| Composition | Cationic lipid | Immediately after mixture of two liquids | | After PBS dialysis | | After 2 months | | After 6 months | | d(nm) |
|---|---|---|---|---|---|---|---|---|---|---|
| | | Average particle diameter (nm) | Polydispersity index | Average particle diameter (nm) | Polydispersity index | Average particle diameter (nm) | Polydispersity index | Average particle diameter (nm) | Polydispersity index | |
| Example 53 | YS-120 | 66.4 | 0.11 | 65.5 | 0.11 | 68.0 | 0.10 | 65.0 | 0.14 | −1.3 |
| Example 54 | YS-124 | 66.7 | 0.14 | 66.9 | 0.11 | 67.2 | 0.13 | 67.2 | 0.11 | 0.5 |
| Comparative Example 3 | ALN-319 | 74.3 | 0.13 | 94.9 | 0.07 | 106.2 | 0.13 | 111.5 | 0.10 | 37.2 |

Preparation (8) of Composition

Example 55

(YS-120)
A composition was prepared using the cationic lipid (YS-120) of Example 16 in the same manner as in the "preparation (6) of composition".

Example 56

(YS-127)
A composition of Example 56 was obtained in the same manner as in Example 55 except that the cationic lipid (YS-127) of Example 23 was used as the cationic lipid in place of YS-120.

Example 57

(YS-128)
A composition of Example 57 was obtained in the same manner as in Example 55 except that the cationic lipid (YS-128) of Example 24 was used as the cationic lipid in place of YS-120.

Example 58

(YS-129)
A composition of Example 58 was obtained in the same manner as in Example 55 except that the cationic lipid (YS-129) of Example 25 was used as the cationic lipid in place of YS-120.

<Analysis (10) of Composition>
In the compositions of Examples 55 to 58, the encapsulation rate of siRNA into the lipid complex and the average particle diameter (Z-average) of the lipid complex were measured in the same manner as those for the composition of Example 29. The encapsulation rate of siRNA and the average particle diameter of the lipid complex are listed in Table 10.

TABLE 10

| Composition | Cationic lipid | Encapsulation rate (%) | Average particle diameter (nm) |
|---|---|---|---|
| Example 55 | YS-120 | 87 | 63 |
| Example 56 | YS-127 | 72 | 80 |
| Example 57 | YS-128 | 84 | 65 |
| Example 58 | YS-129 | 76 | 61 |

Preparation (9) of Composition

Example 59

(YS-101)
A composition was prepared using the cationic lipid (YS-101) of Example 2 in the same manner as in the "preparation (6) of composition".

Example 60

(YS-131)
A composition of Example 60 was obtained in the same manner as in Example 59 except that the cationic lipid (YS-131) of Example 26 was used as the cationic lipid in place of YS-101.

Example 61

(YS-132)
A composition of Example 61 was obtained in the same manner as in Example 59 except that the cationic lipid (YS-132) of Example 27 was used as the cationic lipid in place of YS-101.

Example 62

(YS-133)
A composition of Example 62 was obtained in the same manner as in Example 59 except that the cationic lipid (YS-133) of Example 28 was used as the cationic lipid in place of YS-101.

Example 63

(YS-120)
A composition of Example 63 was obtained in the same manner as in Example 59 except that the cationic lipid (YS-120) of Example 16 was used as the cationic lipid in place of YS-101.

Comparative Example 4

(ALN-319)
A composition of Comparative Example 4 was obtained in the same manner as in Example 59 except that ALN-319 described above was used as the cationic lipid in place of YS-101.

<Analysis (11) of Composition>
In the compositions of Examples 59 to 63 and Comparative Example 4, the encapsulation rate of siRNA into the lipid complex and the average particle diameter (Z-average) of the lipid complex were measured in the same manner as those for the composition of Example 29. The encapsulation rate of siRNA and the average particle diameter of the lipid complex are listed in Table 11.

TABLE 11

| Composition | Cationic lipid | Encapsulation rate (%) | Average particle diameter (nm) |
|---|---|---|---|
| Example 59 | YS-101 | 96 | 70 |
| Example 60 | YS-131 | 92 | 75 |
| Example 61 | YS-132 | 95 | 74 |
| Example 62 | YS-133 | 98 | 71 |
| Example 63 | YS-120 | 97 | 70 |
| Comparative Example 4 | ALN-319 | 97 | 76 |

<Animal Experiment (1)>

Each composition of Examples 29 to 31 and Reference Example 1 was diluted with PBS such that the concentration of Factor VII siRNA encapsulated by the lipid complex was set to 10 µg/mL. Each composition was administered to the tail vein of each C57/BL6 mouse (5 weeks old, male) at a dose volume of 10 mL/kg, and the blood and liver were collected under anesthesia after 24 hours from the administration. The plasma was separated from the blood by centrifugation and the concentration of Factor VII protein in the plasma was quantified using a commercially available kit (trade name "BIOPHEN FVII", HYPHEN BioMed). A group, to which PBS was administered, serving as the negative control was subjected to the same treatment as described above.

The concentration of Factor VII protein of the group to which PBS was administered was set to 100% and the concentration of Factor VII protein of the group to which the composition was administered was calculated as a relative value. Further, the liver was homogenized, the lipids constituting the composition were extracted using methanol, and the cationic lipid was quantified using LC-MS. The amount of administered cationic lipid was set to 100% and the amount of cationic lipid remaining in the liver was calculated as a relative value. The results thereof are listed in Table 12.

TABLE 12

| Amount of siRNA to be administered (mg/kg) | Composition | Cationic lipid | Concentration of Factor VII protein (relative value) | Amount of cationic lipid remaining in liver (relative value) |
|---|---|---|---|---|
| 0.1 | Example 29 | YS-102 | 55% | <1% |
| | Example 30 | YS-101 | 43% | <1% |
| | Example 31 | YS-103 | 11% | 5% |
| | Reference Example 1 | YS-021 | 54% | 56% |

<Animal Experiment (2)>

Each composition of Examples 32 to 37 and Comparative Example 1 was administered to each C57/BL6 mouse (5 weeks old, male) in the same manner as in the "animal experiment (1)", and the relative value of the concentration of Factor VII protein in the plasma after 24 hours from the administration and the relative value of the amount of cationic lipid remaining in the liver were calculated. The results thereof are listed in Table 13.

TABLE 13

| Amount of siRNA to be administered (mg/kg) | Composition | Cationic lipid | Concentration of Factor VII protein (relative value) | Amount of cationic lipid remaining in liver (relative value) |
|---|---|---|---|---|
| 0.1 | Example 32 | YS-111 | 78% | 5% |
| | Example 33 | YS-112 | 19% | 1% |
| | Example 34 | YS-113 | 20% | 25% |
| | Example 35 | YS-114 | 51% | 16% |
| | Example 36 | YS-115 | 32% | <1% |
| | Example 37 | YS-116 | 35% | <1% |
| | Comparative Example 1 | ALN-319 | 22% | <1% |

<Animal Eperiment (3)>

Each composition of Examples 38 to 42 was administered to each C57/BL6 mouse (5 weeks old, male) in the same manner as in the "animal experiment (1)", and the relative value of the concentration of Factor VII protein in the plasma after 24 hours from the administration and the relative value of the amount of cationic lipid remaining in the liver were calculated. The results thereof are listed in Table 14.

TABLE 14

| Amount of siRNA to be administered (mg/kg) | Composition | Cationic lipid | Concentration of Factor VII protein (relative value) | Amount of cationic lipid remaining in liver (relative value) |
|---|---|---|---|---|
| 0.1 | Example 38 | YS-117 | 93% | — |
| | Example 39 | YS-117S | 62% | — |
| | Example 40 | YS-118 | 14% | 10% |
| | Example 41 | YS-118S | 26% | 13% |
| | Example 42 | YS-119 | 5% | <1% |

<Animal Experiment (4)>

Each composition of Example 43 and Comparative Example 2 was diluted with PBS such that the concentration of Factor VII siRNA encapsulated by the lipid complex was set to 1 µg/mL or 5 µg/mL. Each composition was administered to the tail vein of each C57/BL6 mouse (5 weeks old, male) at a dose volume of 10 mL/kg, and the blood and liver were collected under anesthesia after 24 hours from the administration. The plasma was separated from the blood by centrifugation and the concentration of Factor VII protein in the plasma was quantified using a commercially available kit (trade name "BIOPHEN FVII", HYPHEN BioMed). A group, to which PBS was administered, serving as the negative control was subjected to the same treatment as described above.

The concentration of Factor VII protein of the group to which PBS was administered was set to 100% and the concentration of Factor VII protein of the group to which the composition was administered was calculated as a relative value. The results thereof are shown in Table 15 and FIG. 1. It was shown that the composition of Example 43 had higher effects of suppressing expression of Factor VII protein than the composition of Comparative Example 2.

TABLE 15

| Amount of siRNA to be administered (mg/kg) | Composition | Cationic lipid | Concentration of Factor VII protein (relative value) |
|---|---|---|---|
| 0.01 | Example 43 | YS-119 | 57.5% |
| 0.05 | Example 43 | YS-119 | 13.6% |
| 0.01 | Comparative Example 2 | ALN-319 | 83.1% |
| 0.05 | Comparative Example 2 | ALN-319 | 34.6% |

<Animal Experiment (5)>

Each composition of Example 44 and 45 was diluted with PBS such that the concentration of Factor VII siRNA encapsulated by the lipid complex was set to 1 μg/mL or 5 μg/mL. Each composition was administered to the tail vein of each C57/BL6 mouse (5 weeks old, male) at a dose volume of 10 mL/kg, and the blood and liver were collected under anesthesia after 24 hours from the administration. The plasma was separated from the blood by centrifugation and the concentration of Factor VII protein in the plasma was quantified using a commercially available kit (trade name "BIOPHEN FVII", HYPHEN BioMed). A group, to which PBS was administered, serving as the negative control was subjected to the same treatment as described above.

Figure 2:
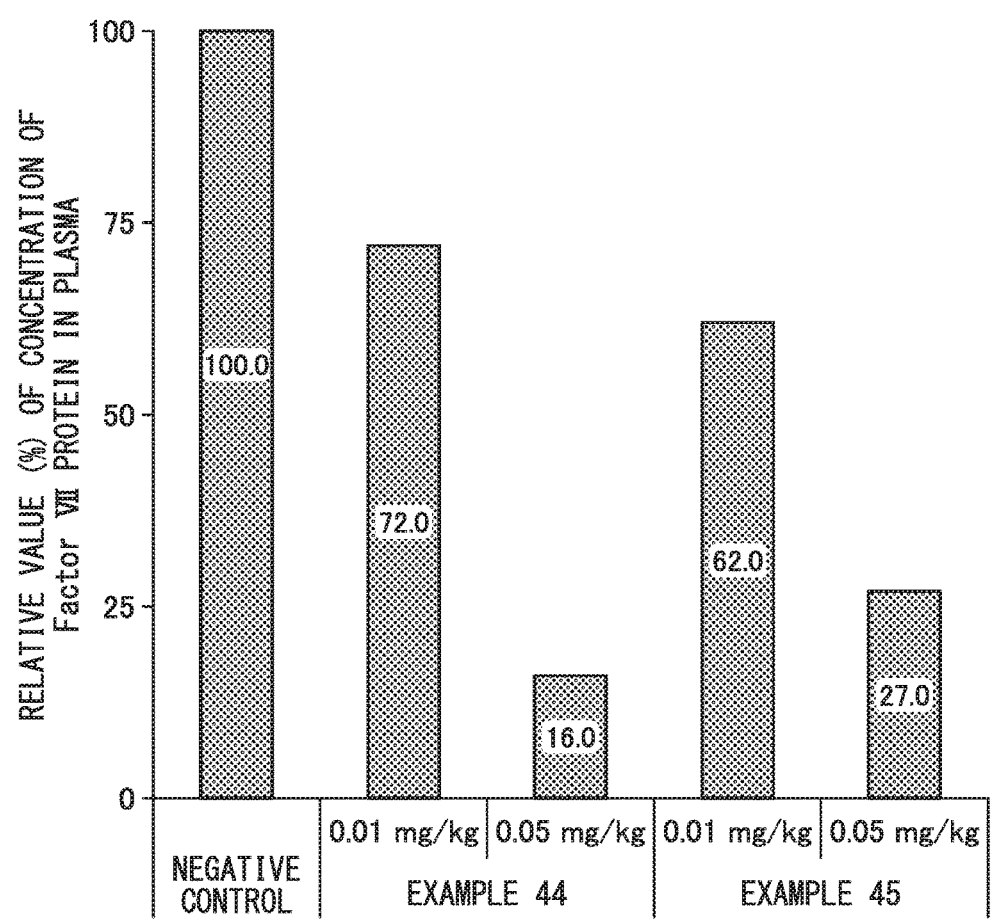
FIG. 2 is a graph showing results of an animal experiment (5).

The concentration of Factor VII protein of the group to which PBS was administered was set to 100% and the concentration of Factor VII protein of the group to which the composition was administered was calculated as a relative value. The results thereof are shown in Table 16 and FIG. 2. It was shown that both of the compositions of Examples 44 and 45 had high effects of suppressing expression of Factor VII protein.

TABLE 16

| Amount of siRNA to be administered (mg/kg) | Composition | Cationic lipid | Concentration of Factor VII protein (relative value) |
|---|---|---|---|
| 0.01 | Example 44 | YS-119 | 72% |
| 0.05 | Example 44 | YS-119 | 16% |
| 0.01 | Example 45 | YS-120 | 62% |
| 0.05 | Example 45 | YS-120 | 27% |

<Animal Experiment (6)>

Each composition of Examples 46 to 52 was administered to each C57/BL6 mouse (5 weeks old, male) in the same manner as in the "animal experiment (5)", and the relative value of the concentration of Factor VII protein in the plasma after 24 hours from the administration was calculated. The results thereof are listed in Table 17.

TABLE 17

| Amount of siRNA to be administered (mg/kg) | Composition | Cationic lipid | Concentration of Factor VII protein (relative value) |
|---|---|---|---|
| 0.01 | Example 46 | YS-120 | 70% |
| | Example 47 | YS-121 | 78% |
| | Example 48 | YS-122 | 66% |
| | Example 49 | YS-123 | 72% |
| | Example 50 | YS-124 | 62% |
| | Example 51 | YS-125 | 73% |
| | Example 52 | YS-126 | 78% |
| 0.05 | Example 46 | YS-120 | 38% |
| | Example 47 | YS-121 | 43% |
| | Example 48 | YS-122 | 35% |
| | Example 49 | YS-123 | 59% |
| | Example 50 | YS-124 | 33% |
| | Example 51 | YS-125 | 46% |
| | Example 52 | YS-126 | 39% |

<Animal Experiment (7)>

Each composition of Examples 53 and 54 and Comparative Example 3 was diluted with PBS such that the concentration of Factor VII siRNA encapsulated by the lipid complex was set to 2 μg/mL or 10 μg/mL. Each composition was administered to the tail vein of each ICR mouse (6 weeks old, female) at a dose volume of 10 mL/kg, and the blood and liver were collected under anesthesia after 24 hours from the administration. The plasma was separated from the blood by centrifugation and the concentration of Factor VII protein in the plasma was quantified using a commercially available kit (trade name "BIOPHEN FVII", HYPHEN BioMed). A group, to which PBS was administered, serving as the negative control was subjected to the same treatment as described above.

The concentration of Factor VII protein of the group to which PBS was administered was set to 100% and the concentration of Factor VII protein of the group to which the composition was administered was calculated as a relative value. The results thereof are listed in Table 18. It was shown that the compositions of Examples 53 and 54 had higher effects of suppressing expression of Factor VII protein than the composition of Comparative Example 3.

TABLE 18

| Amount of siRNA to be administered (mg/kg) | Composition | Cationic lipid | Concentration of Factor VII protein (relative value) |
|---|---|---|---|
| 0.02 | Example 53 | YS-120 | 53% |
| | Example 54 | YS-124 | 51% |
| | Comparative Example 3 | ALN-319 | 82% |
| 0.1 | Example 53 | YS-120 | 17% |
| | Example 54 | YS-124 | 15% |
| | Comparative Example 3 | ALN-319 | 37% |

<Animal Experiment (8)>

Each composition of Examples 55 to 58 was administered to each ICR mouse (6 weeks old, female) in the same manner as in the "animal experiment (7)", and the relative value of the concentration of Factor VII protein in the plasma after 24 hours from the administration was calculated. The results thereof are listed in Table 19.

TABLE 19

| Amount of siRNA to be administered (mg/kg) | Composition | Cationic lipid | Concentration of Factor VII protein (relative value) |
|---|---|---|---|
| 0.02 | Example 56 | YS-127 | 78% |
| | Example 57 | YS-128 | 52% |
| | Example 58 | YS-129 | 65% |
| | Example 55 | YS-120 | 59% |

TABLE 19-continued

| Amount of siRNA to be administered (mg/kg) | Composition | Cationic lipid | Concentration of Factor VII protein (relative value) |
|---|---|---|---|
| 0.1 | Example 56 | YS-127 | 63% |
|  | Example 57 | YS-128 | 20% |
|  | Example 58 | YS-129 | 35% |
|  | Example 55 | YS-120 | 18% |

<Animal Experiment (9)>

Each composition of Examples 59 to 63 and Comparative Example 4 was administered to each ICR mouse (5 weeks old, female) in the same manner as in the "animal experiment (7)", and the relative value of the concentration of Factor VII protein in the plasma after 24 hours from the administration was calculated. The results thereof are listed in Table 20.

TABLE 20

| Amount of siRNA to be administered (mg/kg) | Composition | Cationic lipid | Concentration of Factor VII protein (relative value) |
|---|---|---|---|
| 0.01 | Example 59 | YS-101 | 71% |
| 0.02 | Example 60 | YS-131 | 102% |
|  | Example 61 | YS-132 | 78% |
|  | Example 62 | YS-133 | 33% |
|  | Example 63 | YS-120 | 38% |
|  | Comparative Example 4 | ALN-319 | 57% |
| 0.03 | Example 59 | YS-101 | 24% |
| 0.1 | Example 59 | YS-101 | 11% |
|  | Example 60 | YS-131 | 72% |
|  | Example 61 | YS-132 | 18% |
|  | Example 62 | YS-133 | 8% |
|  | Example 63 | YS-120 | 7% |
|  | Comparative Example 4 | ALN-319 | 14% |

INDUSTRIAL APPLICABILITY

According to the present invention, it is possible to provide a cationic lipid capable of efficiently releasing a nucleic acid to the cytoplasm.

---

The invention claimed is:

1. A compound selected from the group consisting of compounds represented by the following Formulae (1) to (11) or a pharmaceutically acceptable salt thereof

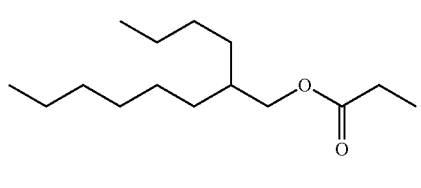

(1)

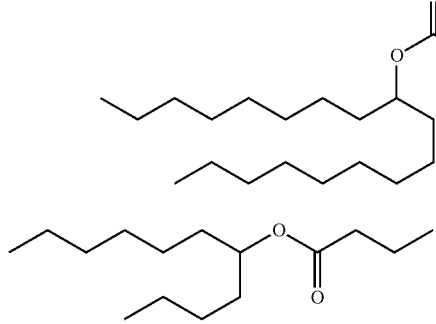

(2)

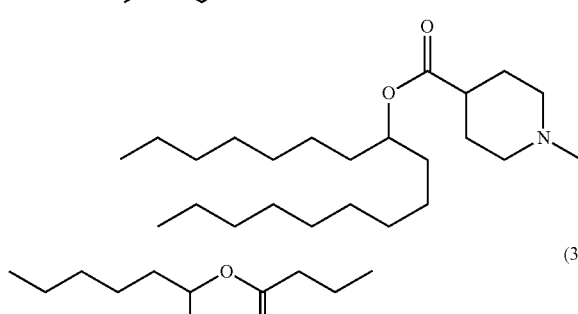

(3)

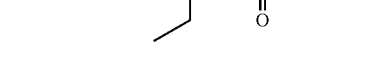

-continued

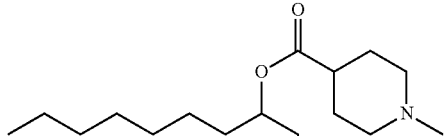

(4)

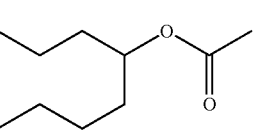

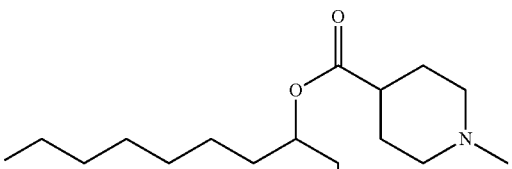

(5)

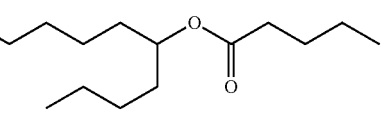

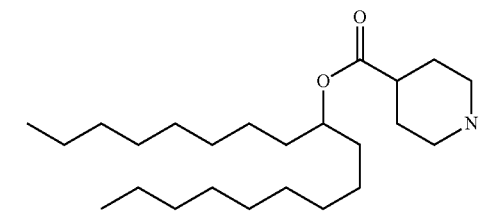

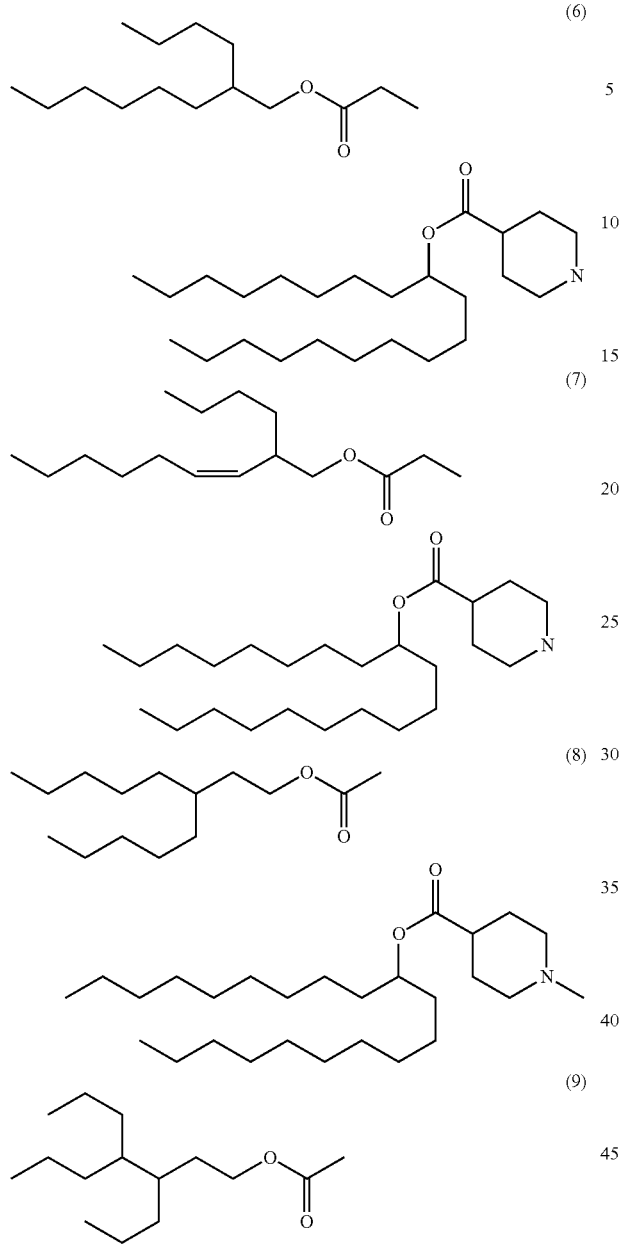
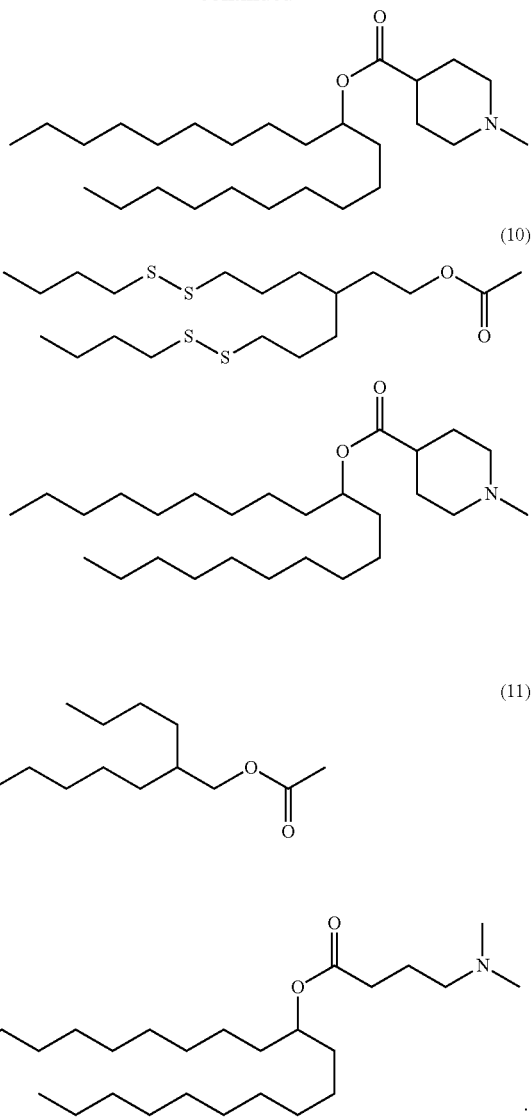
2. The compound according to claim 1 selected from the group consisting of compounds represented by the following Formulae (1) and (6) to (9) or a pharmaceutically acceptable salt thereof
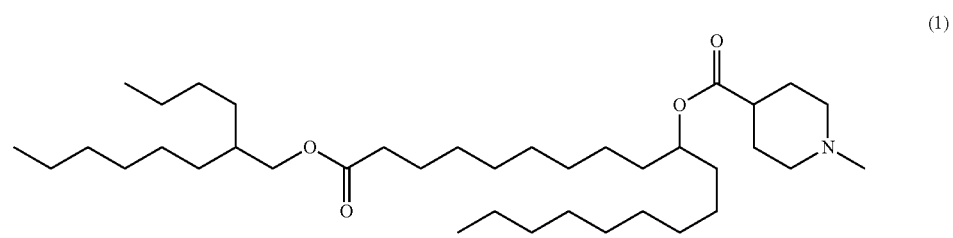

(6)
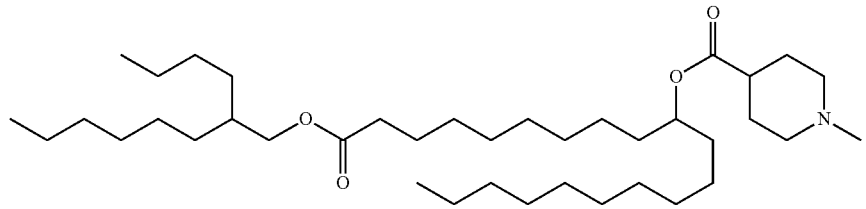
(7)
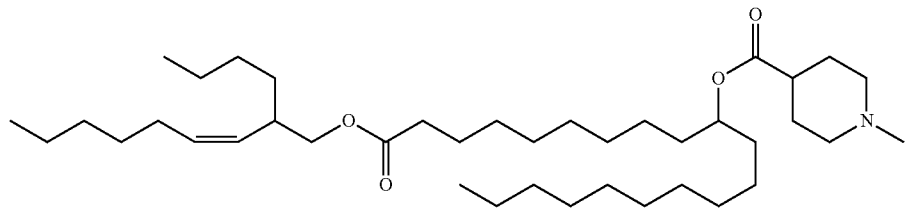
(8)
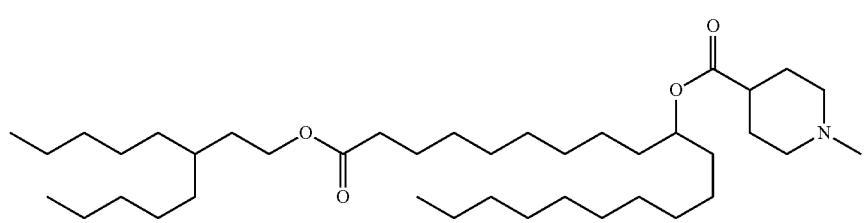
(9)
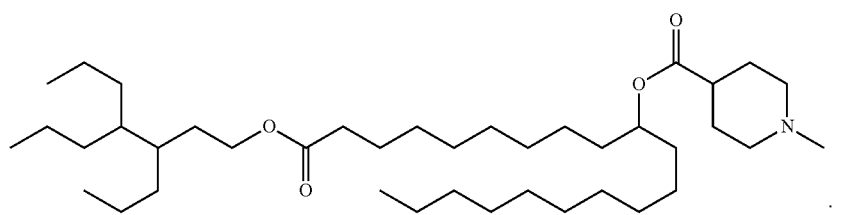
3. The compound according to claim 1 represented by the following Formula (1) or a pharmaceutically acceptable salt thereof
(1)
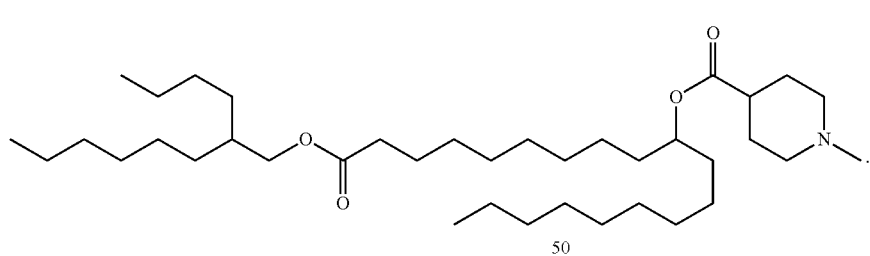
4. The compound according to claim 1 represented by the following Formula (6) or a pharmaceutically acceptable salt thereof
(6)
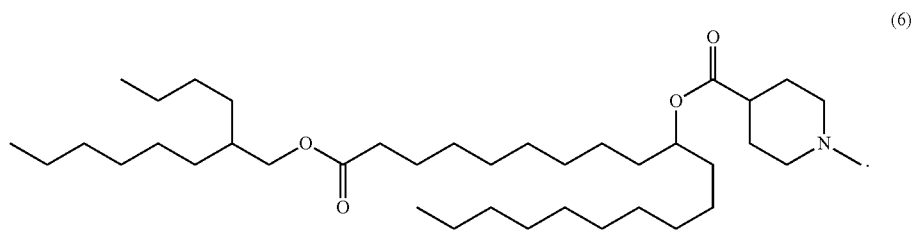 [SMILES: CCCCCCCCCCC(CCCCCCCCC(=O)OCC(CCCC)CCCCCC)OC(=O)C1CCN(C)CC1]

5. The compound according to claim 1 represented by the following Formula (8) or a pharmaceutically acceptable salt thereof

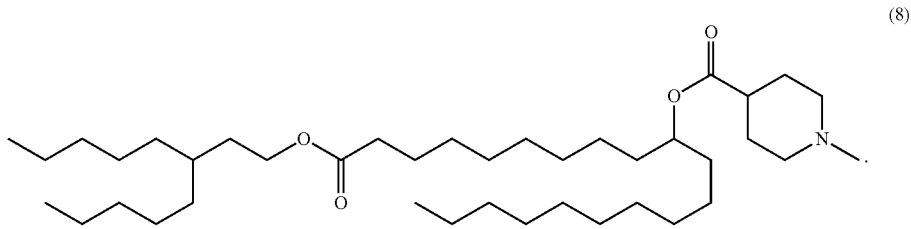 [SMILES: CCCCCCCCCCC(CCCCCCCCC(=O)OCCC(CCCCC)CCCCC)OC(=O)C1CCN(C)CC1]

6. A lipid complex comprising:
(I) the compound according to claim 1 or a pharmaceutically acceptable salt thereof; and
(II) at least one lipid selected from the group consisting of a neutral lipid, a polyethylene glycol-modified lipid, and a sterol.

7. A composition comprising:
(I) the compound according to claim 1 or a pharmaceutically acceptable salt thereof;
(II) at least one lipid selected from the group consisting of a neutral lipid, a polyethylene glycol-modified lipid, and a sterol; and
(III) nucleic acid.

8. A method of producing a composition, comprising:
a process of mixing a polar organic solvent-containing aqueous solution which contains (I) the compound according to claim 1 or a pharmaceutically acceptable salt thereof, and (II) at least one lipid selected from the group consisting of a neutral lipid, a polyethylene glycol-modified lipid, and a sterol, and (III) an aqueous solution which contains nucleic acid, so as to obtain a mixed solution; and
a process of decreasing the content of the polar organic solvent in the mixed solution.

* * * * *

UNITED STATES PATENT AND TRADEMARK OFFICE
CERTIFICATE OF CORRECTION

PATENT NO. : 10,081,598 B2
APPLICATION NO. : 15/533576
DATED : September 25, 2018
INVENTOR(S) : Yuta Suzuki, Kenji Hyodo and Yohei Tanaka Page 1 of 7

It is certified that error appears in the above-identified patent and that said Letters Patent is hereby corrected as shown below:

In the Claims

Column 63

Claim 1, Lines 32-47, delete " 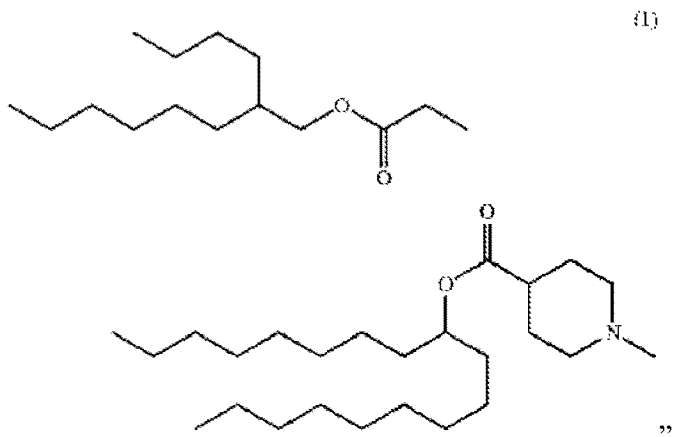 "

and insert -- 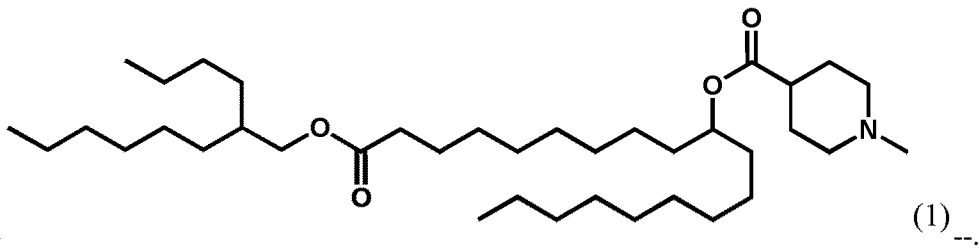 --.

Signed and Sealed this
Thirty-first Day of December, 2019

Andrei Iancu
*Director of the United States Patent and Trademark Office*

CERTIFICATE OF CORRECTION (continued)
U.S. Pat. No. 10,081,598 B2

Column 63

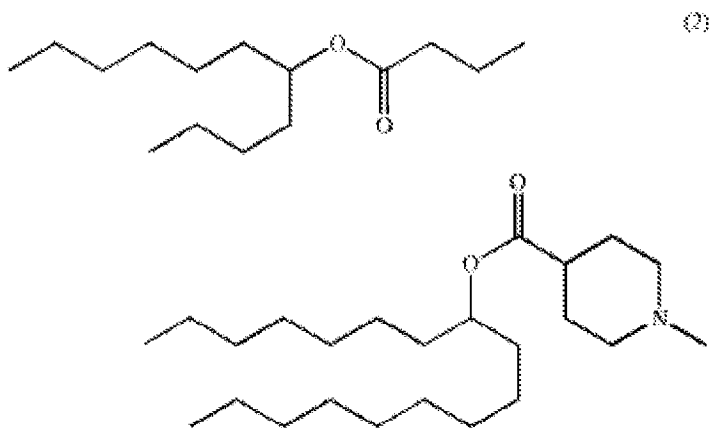

Claim 1, Lines 48-60, delete " 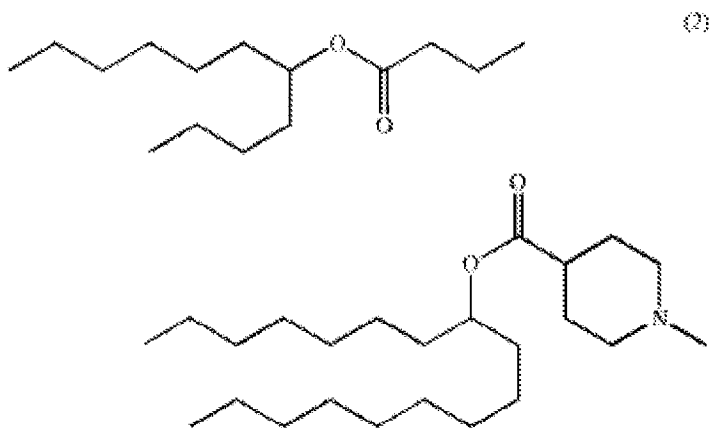 " and
insert -- 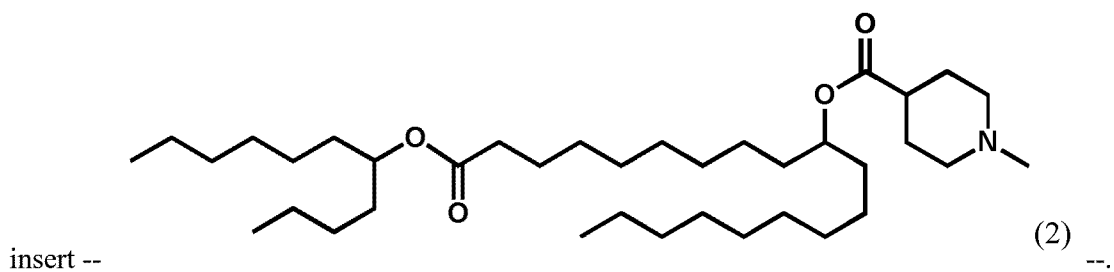 (2) --.

Column 63 and 64
Claim 1, Column 63, Lines 61-65; and Column 64, Lines 27-34 delete

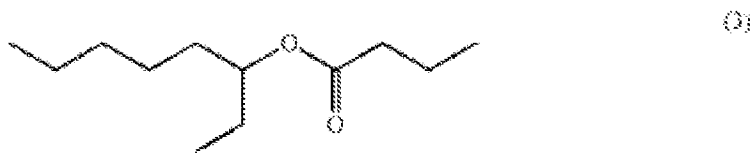

" 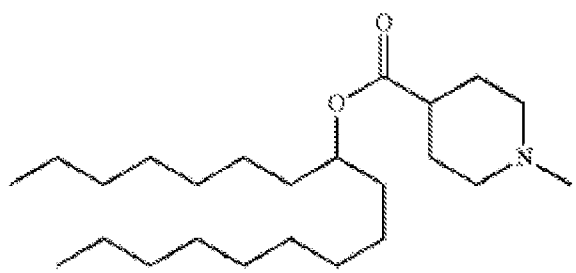 " and insert

-- 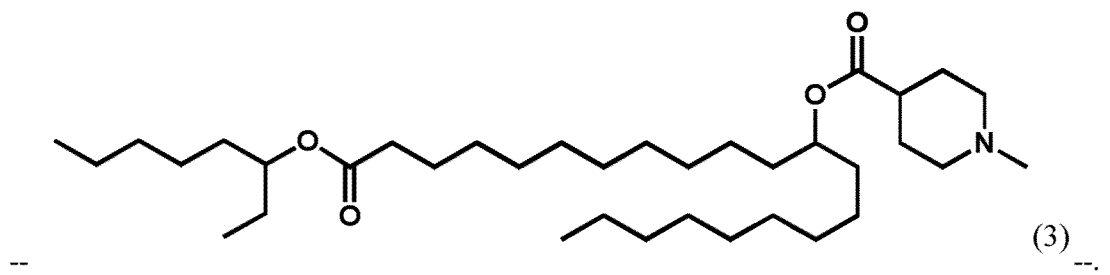 (3) --.

CERTIFICATE OF CORRECTION (continued)
U.S. Pat. No. 10,081,598 B2

Column 64

Claim 1, Lines 35-50, delete " 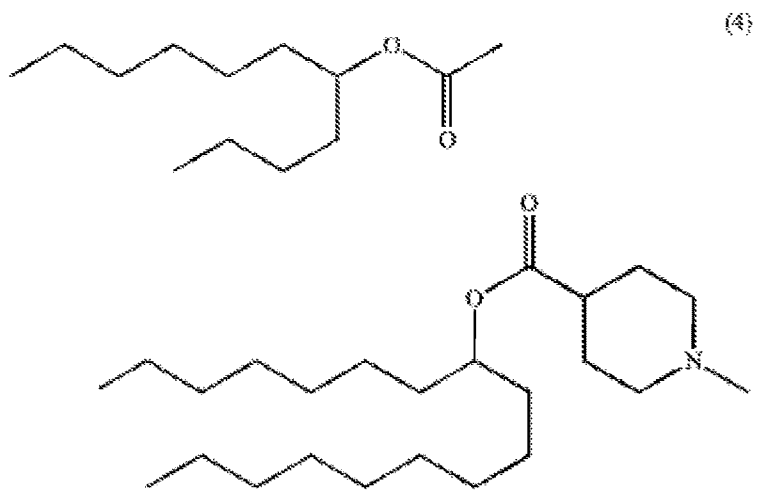 " and insert -- 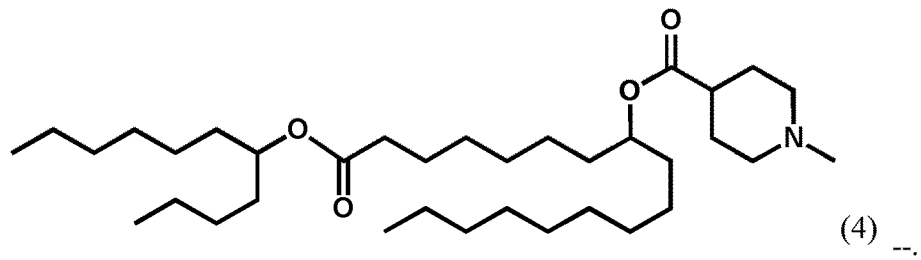 (4) --.

Column 64

Claim 1, Lines 51-66, delete " 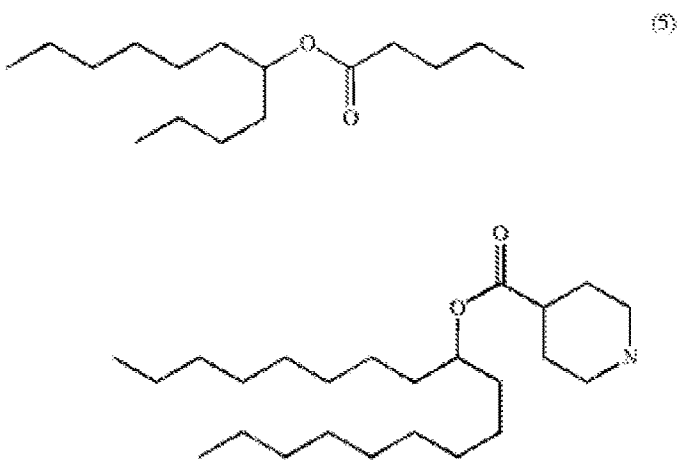 " and insert -- 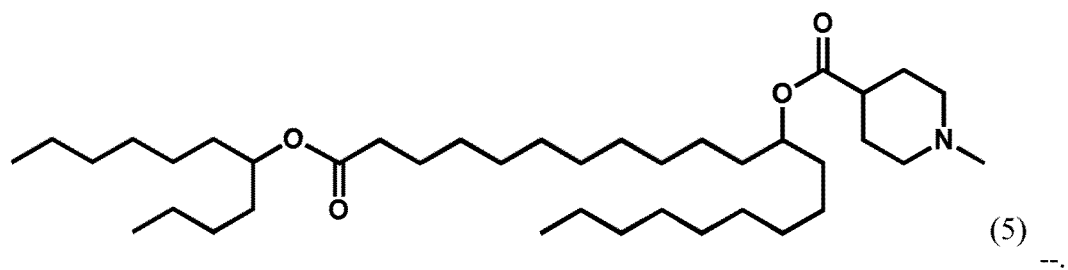 --.

CERTIFICATE OF CORRECTION (continued)
U.S. Pat. No. 10,081,598 B2

Column 65

Claim 1, Lines 1-15, delete " 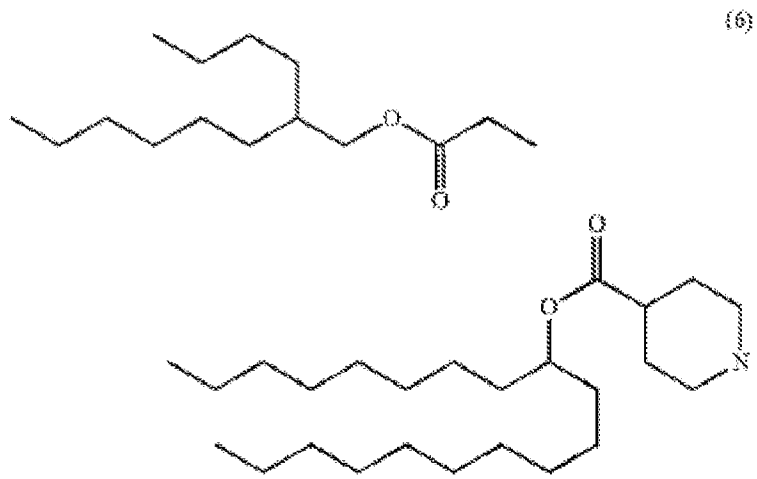 " and insert -- 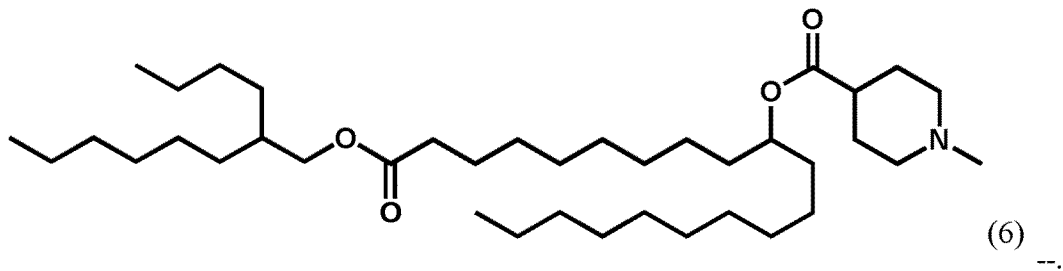 --.

Column 65

Claim 1, Lines 16-29, delete " 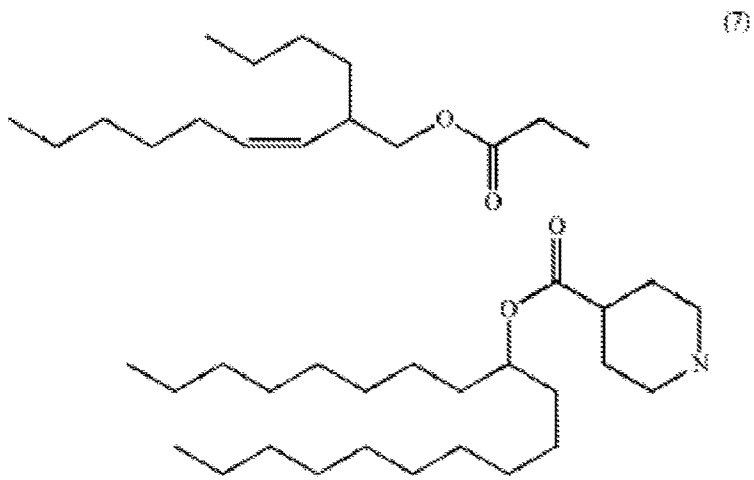 " and insert -- 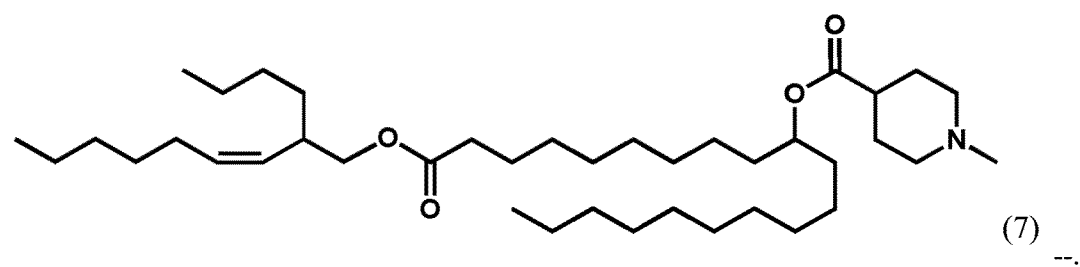 --.

Column 65
Claim 1, Lines 30-41, delete " 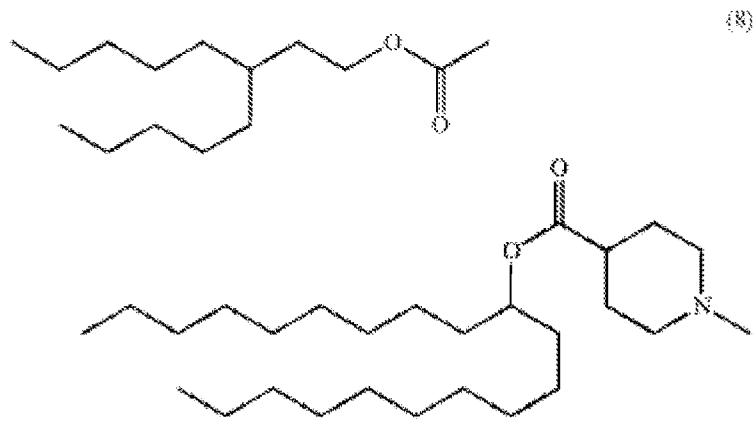 " and insert -- 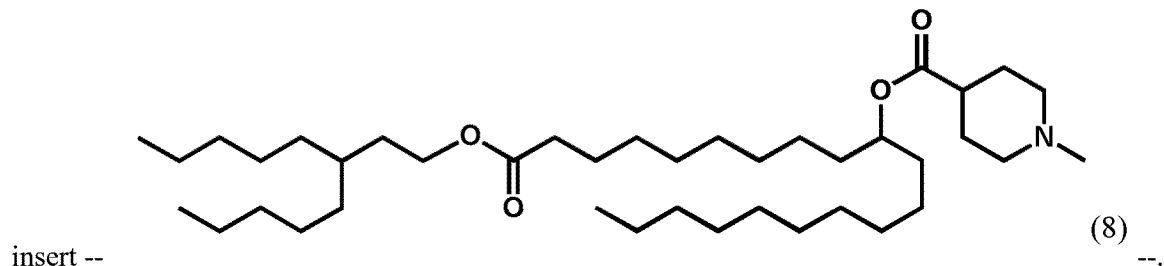 --.
Columns 65 and 66
Claim 1, Column 65, Lines 42-49; and Column 66, Lines 1-9 delete
" 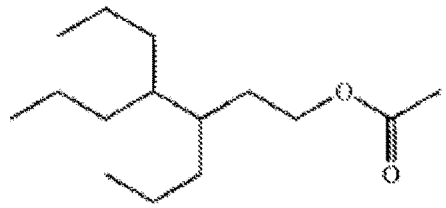
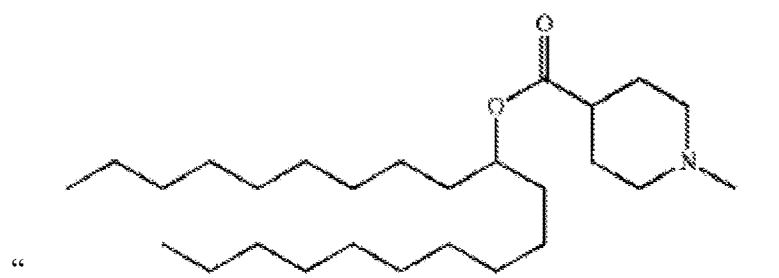 " and insert

CERTIFICATE OF CORRECTION (continued)
U.S. Pat. No. 10,081,598 B2

--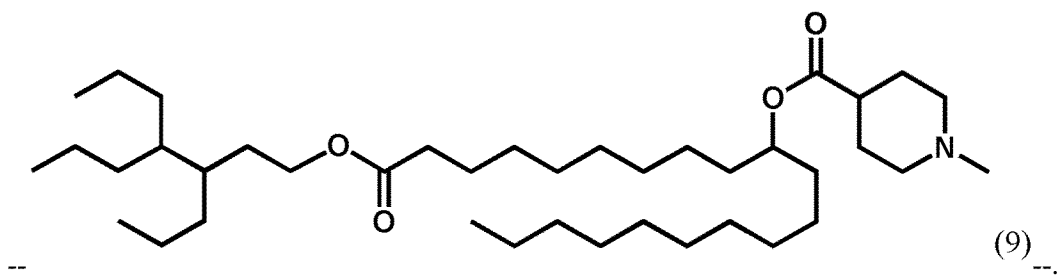--.

Column 66

Claim 1, Lines 10-25, delete " 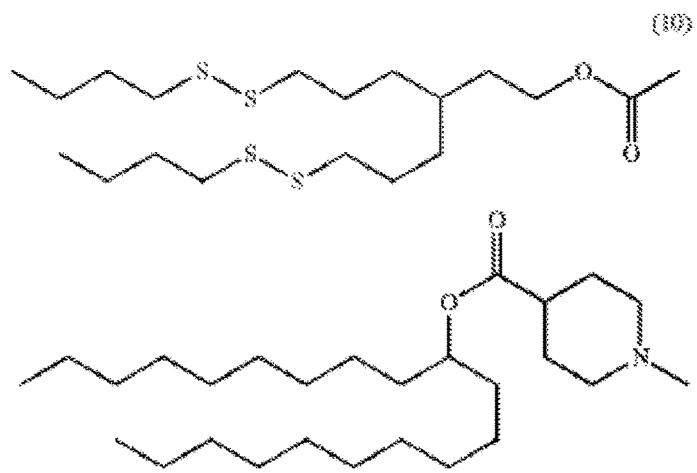 " and insert -- 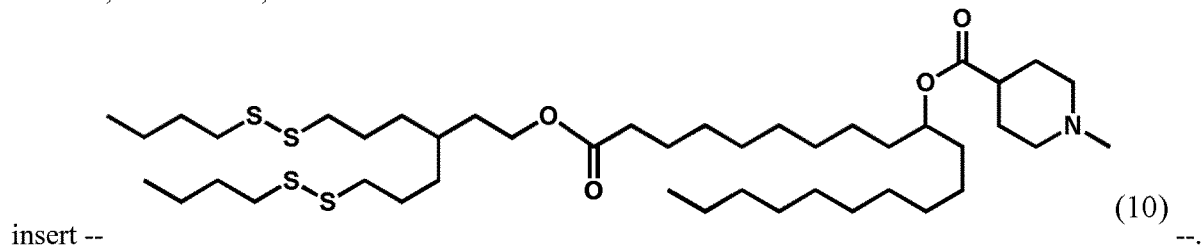 --.

CERTIFICATE OF CORRECTION (continued)
U.S. Pat. No. 10,081,598 B2

Column 66

Claim 1, Lines 27-44, delete " 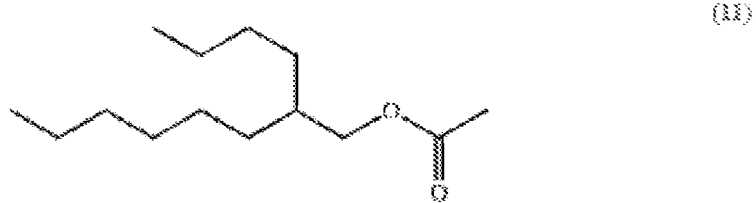 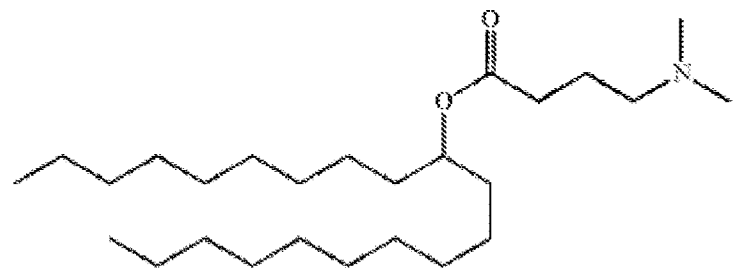 " and insert -- 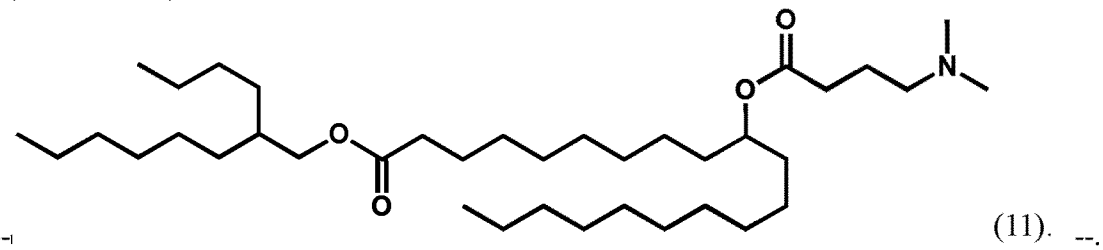 (11). --.